US012740763B2

(12) United States Patent
Khokhlova et al.

(10) Patent No.: US 12,740,763 B2
(45) Date of Patent: Sep. 22, 2026

(54) TREATMENT PLANNING AND ABERRATION CORRECTION ALGORITHMS FOR HIGH INTENSITY FOCUSED ULTRASOUND (HIFU) ABLATION OF SOFT TISSUE TARGETS

(71) Applicant: UNIVERSITY OF WASHINGTON, Seattle, WA (US)

(72) Inventors: Tatiana D. Khokhlova, Seattle, WA (US); Vera A. Khokhlova, Seattle, WA (US); Pavel Rosnitskiy, Seattle, WA (US); Oleg A. Sapozhnikov, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 19/295,387

(22) Filed: Aug. 8, 2025

(65) Prior Publication Data

US 2026/0041400 A1 Feb. 12, 2026

Related U.S. Application Data

(60) Provisional application No. 63/681,309, filed on Aug. 9, 2024.

(51) Int. Cl.
*A61B 8/00* (2006.01)

(52) U.S. Cl.
CPC .......... *A61B 8/4494* (2013.01); *A61B 8/5223* (2013.01)

(58) Field of Classification Search
CPC ..... A61B 8/4494; A61B 8/5223; A61B 34/10; A61B 8/085; A61B 8/4488; A61B 2034/101; A61N 7/02; A61N 2007/0095
See application file for complete search history.

(56) References Cited

U.S. PATENT DOCUMENTS 5,134,288 A * 7/1992 Van Dijck ............. H01J 37/222 250/311
6,485,423 B2 * 11/2002 Angelsen ............ G01S 7/52038 600/443

(Continued)

OTHER PUBLICATIONS

P. B. Rosnitskiy, P. V. Yuldashev, O. A. Sapozhnikov, L. R. Gavrilov, and V. A. Khokhlova, "Simulation of nonlinear trans-skull focusing and formation of shocks in brain using a fully populated ultrasound array with aberration correction," Journal of the Acoustical Society of America, vol. 146, No. 3, pp. 1786-1798, 2019.

(Continued)

*Primary Examiner* — Bo Joseph Peng
(74) *Attorney, Agent, or Firm* — Christensen O'Connor Johnson Kindness PLLC

(57) ABSTRACT

Treatment planning and aberration correction algorithms for high intensity focused ultrasound (Hifu) ablation of soft tissue targets, and associated systems and methods are described. In one embodiment, a method for planning a sonication treatment of a target in a body includes obtaining a 3D anatomical model of the target and a portion of the body that is disposed between an ultrasound transducer and the target, where the ultrasound transducer is a phased array ultrasound transducer comprising a plurality of elements. The method also includes: selecting a position of the ultrasound transducer by applying a transducer positioning algorithm for optimizing a sonication geometry; and simulating an aberrated ultrasound field at the target, where the aberrated ultrasound field is a linear high-intensity focused ultrasound (HIFU) field. The method also includes compensating for phase aberrations of the aberrated ultrasound field by: backpropagating an ultrasound field from a virtual point source at the target, through the portion of the body that is disposed between the ultrasound transducer and the target, toward the ultrasound transducer, where the ultrasound field (Continued)

is spherical at the virtual point; and, based on backpropagating the ultrasound field from the virtual point, determining time delays at the elements of the ultrasound transducer, where the time delays are configured for compensating the phase aberrations of the ultrasound field at the virtual point source.

22 Claims, 16 Drawing Sheets
(9 of 16 Drawing Sheet(s) Filed in Color)

(56) References Cited

U.S. PATENT DOCUMENTS

2014/0135681 A1* 5/2014 Angelsen ................ A61N 7/00 604/22
2025/0090871 A1* 3/2025 Snell ........................ A61N 7/00

OTHER PUBLICATIONS

P. B. Rosnitskiy, B. A. Vysokanov, L. R. Gavrilov, O. A. Sapozhnikov, and V. A. Khokhlova, "Method for designing multielement fully populated random phased arrays for ultrasound surgery applications," IEEE Transactions on Ultrasonics, Ferroelectrics, and Frequency Control, vol. 65, No. 4, pp. 630-637, 2018.
C. Ewertsen, A. Săftoiu, L. G. Gruionu, S. Karstrup, and M. B. Nielsen, "Real-Time Image Fusion Involving Diagnostic Ultrasound," American Journal of Roentgenology, vol. 200, No. 3, pp. W249-W255, Mar. 2013.
G. ter Haar and C. Coussios, "High intensity focused ultrasound: Physical principles and devices," Int. J. Hyperthermia, vol. 23, No. 2, pp. 89-104, Jan. 2007.
R. P. Williams, J. C. Simon, V. A. Khokhlova, O. A. Sapozhnikov, and T. D. Khokhlova, "The histotripsy spectrum: differences and similarities in techniques and instrumentation," International Journal of Hyperthermia, vol. 40, No. 1, Jul. 2023.
M. O'Donnell and S. W. Flax, "Phase-aberration correction using signals from point reflectors and diffuse scatterers: Measurements," IEEE Trans. Ultrason., Ferroelectr., Freq. Control, vol. UFFC-35, No. 6, pp. 768-774, Nov. 1988.
L. M. Hinkelman, T. D. Mast, L. A. Metlay, and R. C. Waag, "The effect of abdominal wall morphology on ultrasonic pulse distortion. Part I. Measurements," J. Acoust. Soc. Amer., vol. 104, No. 6, pp. 3635-3649, Dec. 1998.
V. Amin, R. Roberts, T. Long, R. B. Thompson, and T. Ryken, "A study of effects of tissue inhomogeneity on HIFU beam," AIP Conf., vol. 829, No. 1, pp. 201-205, 2006.
J.-F. Aubry, M. Pernot, F. Marquet, M. Tanter, and M. Fink, "Transcostal high-intensity-focused ultrasound: Ex vivo adaptive focusing feasibility study," Phys. Med. Biol., vol. 53, No. 11, p. 2937, 2008.
T. D. Khokhlova et al., "Pilot in vivo studies on transcutaneous boiling histotripsy in porcine liver and kidney," Sci. Rep., vol. 9, No. 1, pp. 1-12, Dec. 2019.
E. Yeats, D. Gupta, Z. Xu, and T. L. Hall, "Effects of phase aberration on transabdominal focusing for a large aperture, low f-number histotripsy transducer," Phys. Med. Biol, vol. 67, No. 15, p. 155004, Jul. 19, 2022.
R. W. Ritchie et al., "Extracorporeal high intensity focused ultrasound for renal tumours: a 3-year follow-up," BJU International, vol. 106, No. 7. Wiley, pp. 1004-1009, Sep. 14, 2010.
D. Cranston, T. Leslie, and G. ter Haar, "A Review of High-Intensity Focused Ultrasound in Urology," Cancers, vol. 13, No. 22, p. 5696, Nov. 14, 2021.
R. Ritchie, J. Collin, C. Coussios, and T. Leslie, "Attenuation and defocusing during high-intensity focused ultrasound therapy through perinephric fat," Ultrasound Med. Biol., vol. 39, No. 10, pp. 1785-1793, Oct. 2013.
J. Jaros, A. P. Rendell, and B. E. Treeby, "Full-wave nonlinear ultrasound simulation on distributed clusters with applications in high-intensity focused ultrasound," The International Journal of High Performance Computing Applications, vol. 30, No. 2, pp. 137-155, Apr. 29, 2015.
V. Suomi, J. Jaros, B. Treeby, and R. Cleveland, "Nonlinear 3-D simulation of high-intensity focused ultrasound therapy in the Kidney," 38th Annual International Conference of the IEEE Engineering in Medicine and Biology Society, pp. 5648-5651 Aug. 2016.
H. Liu, N. McDannold, and K. Hynynen, "Focal beam distortion and treatment planning in abdominal focused ultrasound surgery," Medical Physics, vol. 32, No. 5. Wiley, pp. 1270-1280, Apr. 14, 2005.
A. S. Bobina, P. B. Rosnitskiy, T. D. Khokhlova, P. V. Yuldashev, and V. A. Khokhlova, "Effect of Abdominal Wall Inhomogeneities on the Focusing of an Ultrasonic Beam at Different Positions of the Transducer," Bulletin of the Russian Academy of Sciences: Physics, vol. 85, No. 6, pp. 675-680, Jun. 2021.
M. Mancini, M. Righetto, and G. Baggio, "Gender-Related Approach to Kidney Cancer Management: Moving Forward," International Journal of Molecular Sciences, vol. 21, No. 9, p. 3378, May 10, 2020.
R. O. Illing et al., "The safety and feasibility of extracorporeal high-intensity focused ultrasound (HIFU) for the treatment of liver and kidney tumours in a Western population," British Journal of Cancer, vol. 93, No. 8, pp. 890-895, Sep. 27, 2005.
K. Hynynen and R. M. Jones, "Image-guided ultrasound phased arrays are a disruptive technology for non-invasive therapy," Physics in Medicine and Biology, vol. 61, No. 17, pp. R206-R248, Aug. 5, 2016.
T. Bancel et al., "Comparison Between Ray-Tracing and Full-Wave Simulation for Transcranial Ultrasound Focusing on a Clinical System Using the Transfer Matrix Formalism," IEEE Trans. Ultrason., Ferroelectr., Freq. Control, vol. 68, No. 7., pp. 2554-2565, Jul. 2021.
A. Kyriakou, E. Neufeld, B. Werner, M. M. Paulides, G. Szekely, and N. Kuster, "A review of numerical and experimental compensation techniques for skull-induced phase aberrations in transcranial focused ultrasound," International Journal of Hyperthermia, vol. 30, No. 1, pp. 36-46, Dec. 10, 2013.
F. Marquet et al., "Non-invasive transcranial ultrasound therapy based on a 3D CT scan: protocol validation and in vitro results," Physics in Medicine and Biology, vol. 54, No. 9. pp. 2597-2613, Apr. 2009.
A. I. Farrer et al., "Phase aberration simulation study of MRgFUS breast treatments," Medical Physics, vol. 43, No. 3. Wiley, pp. 1374-1384, Feb. 23, 2016.
R. Narumi et al., "Focus Control Aided by Numerical Simulation in Heterogeneous Media for High-Intensity Focused Ultrasound Treatment," Japanese Journal of Applied Physics, vol. 52, No. 7S, p. 07HF01, Jun. 20, 2013.
C. Moonen, and M. Ries, "High intensity focused ultrasound with large aperture transducers: A MRI based focal point correction for tissue heterogeneity," Medical Physics, vol. 39, No. 4, pp. 1936-1945, Mar. 19, 2012.
Y. Jing, F. C. Meral, and G. T. Clement, "Time-reversal transcranial ultrasound beam focusing using a k-space method," Physics in Medicine and Biology, vol. 57, No. 4, pp. 901-917, Jan. 31, 2012.
S. Bobkova, L. Gavrilov, V. Khokhlova, A. Shaw, and J. Hand, "Focusing of High-Intensity Ultrasound Through the Rib Cage Using a Therapeutic Random Phased Array," Ultrasound in Medicine and Biology, vol. 36, No. 6, pp. 888-906, Jun. 2010.
M. Pernot, G. Montaldo, M. Tanter, and M. Fink, "Ultrasonic stars" for time-reversal focusing using induced cavitation bubbles, Applied Physics Letters, vol. 88, No. 3, Jan. 16, 2006.
J. J. Macoskey et al., "Soft-Tissue Aberration Correction for Histotripsy," IEEE Trans. Ultrason., Ferroelectr., Freq. Control, vol. 65, No. 11., pp. 2073-2085, Nov. 2018.
G. P. L. Thomas, T. D. Khokhlova, O. A. Sapozhnikov, Y.-N. Wang, S. I. Totten, and V. A. Khokhlova, "In Vivo Aberration Correction for Transcutaneous HIFU Therapy Using a Multielement Array," IEEE Trans. Ultrason., Ferroelectr., Freq. Control, vol. 69, No. 10, pp. 2955-2964, Oct. 2022.

(56) References Cited

OTHER PUBLICATIONS

G. P. L. Thomas, T. D. Khokhlova, O. A. Sapozhnikov, and V. A. Khokhlova, "Enhancement of Boiling Histotripsy by Steering the Focus Axially During the Pulse Delivery," IEEE Trans. Ultrason., Ferroelectr., Freq. Control, vol. 70, No. 8, pp. 865-875, Aug. 2023.
N. Lu et al., "Two-step aberration correction: application to transcranial histotripsy," Physics in Medicine & Biology, vol. 67, No. 12, p. 125009, Jun. 10, 2022.
B. E. Treeby, E. S. Wise, F. Kuklis, J. Jaros, and B. T. Cox, "Nonlinear ultrasound simulation in an axisymmetric coordinate system using a k-space pseudospectral method," The Journal of the Acoustical Society of America, vol. 148, No. 4, pp. 2288-2300, Oct. 1, 2020.
M. Cudova, B. E. Treeby, and J. Jaros, "Design of HIFU treatment plans using an evolutionary strategy," Proceedings of the Genetic and Evolutionary Computation Conference Companion, Jul. 6, 2018.
P. B. Rosnitskiy, P. V. Yuldashev, O. A. Sapozhnikov, A. D. Maxwell, W. Kreider, M. R. Bailey, and V. A. Khokhlova, "Design of HIFU transducers for generating specified nonlinear ultrasound fields," IEEE Transactions on Ultrasonics, Ferroelectrics, and Frequency Control, vol. 64, No. 2, pp. 374-390, 2017.
M. Schwenke, J. Georgii and T. Preusser, "Fast Numerical Simulation of Focused Ultrasound Treatments During Respiratory Motion With Discontinuous Motion Boundaries," IEEE Transactions on Biomedical Engineering, vol. 64, No. 7, pp. 1455-1468, Jul. 2017.
V. A. Khokhlova et al., "Design of HIFU transducers to generate specific nonlinear ultrasound fields," Phys. Procedia, vol. 87, pp. 132-138, Jan. 2016.
M. A. Ghanem et al., "Field characterization and compensation of vibrational nonuniformity for a 256-element focused ultrasound phased array," IEEE Trans. Ultrason., Ferroelectr., Freq. Control, vol. 65, No. 9, pp. 1618-1630, Sep. 2018.
C. R. Bawiec et al., "A Prototype Therapy System for Boiling Histotripsy in Abdominal Targets Based on a 256-Element Spiral Array," IEEE Transactions on Ultrasonics, Ferroelectrics, and Frequency Control, vol. 68, No. 5, pp. 1496-1510, May 2021.
M. A. Ghanem et al., "Noninvasive acoustic manipulation of objects in a living body," Proceedings of the National Academy of Sciences, vol. 117, No. 29. Proceedings of the National Academy of Sciences, pp. 16848-16855, Jul. 6, 2020.
J. L. B. Robertson, B. T. Cox, J. Jaros, and B. E. Treeby, "Accurate simulation of transcranial ultrasound propagation for ultrasonic neuromodulation and stimulation," J. Acoust. Soc. Am., vol. 141, No. 3, pp. 1726-1738, Mar. 2017.
U. Schneider, E. Pedroni, and A. Lomax, "The calibration of CT Hounsfield units for radiotherapy treatment planning," Physics in Medicine and Biology, vol. 41, No. 1, pp. 111-124, Jan. 1996.
T. D. Mast, "Empirical relationships between acoustic parameters in human soft tissues," Acoustics Research Letters Online, vol. 1, No. 2, pp. 37-42, Oct. 2000.
C. R. Bawiec, p. B. Rosnitskiy, A. T. Peek, A. D. Maxwell, W. Kreider, G. R. ter Haar, O. A. Sapozhnikov, V. A. Khokhlova, and T. D. Khokhlova, "Inertial cavitation behaviors induced by nonlinear focused ultrasound pulses," IEEE Transactions on Ultrasonics, Ferroelectrics, and Frequency Control, vol. 68, No. 9, pp. 2884-2895, 2021.
J. C. Lagarias, J. A. Reeds, M. H. Wright, and P. E. Wright, "Convergence Properties of the Nelder-Mead Simplex Method in Low Dimensions," SIAM Journal on Optimization, vol. 9, No. 1. Society for Industrial & Applied Mathematics (SIAM), pp. 112-147, Jan. 1998.
B. E. Treeby and B. T. Cox, "k-Wave: MATLAB toolbox for the simulation and reconstruction of photoacoustic wave fields," Journal of Biomedical Optics, vol. 15, No. 2, p. 021314, 2010.
B.E. Treeby, B.T. Cox, and J. Jaros, "k-Wave—A Matlab Toolbox for the Time Domain Simulation of Acoustic Wave Fields: User Manual," 2012. [Online]. Available: http://www.k-wave.org.
B. E. Treeby, J. Jaros, A. P. Rendell, and B. T. Cox, "Modeling nonlinear ultrasound propagation in heterogeneous media with power law absorption using a k-space pseudospectral method," J. Acoust. Soc. Am. vol. 131, pp. 4324-4336, 2012.
O. A. Sapozhnikov, S. A. Tsysar, V. A. Khokhlova, and W. Kreider, "Acoustic holography as a metrological tool for characterizing medical ultrasound sources and fields," Journal of the Acoustical Society of America, vol. 138, No. 3, pp. 1515-1532, 2015.
J.-F. Aubry, M. Tanter, M. Pernot, J.-L. Thomas, and M. Fink, "Experimental demonstration of noninvasive transskull adaptive focusing based on prior computed tomography scans," The Journal of the Acoustical Society of America, vol. 113, No. 1, pp. 84-93, Jan. 1, 2003.
S. A. Ilyin, P. V. Yuldashev, V. A. Khokhlova, L. R. Gavrilov, P. B. Rosnitskiy, and O. A. Sapozhnikov, "Analytical method for evaluating the quality of acoustic fields radiated by a multielement therapeutic array with electronic focus steering," Acoustical Physics, vol. 61, No. 1, pp. 52-59, 2015.

* cited by examiner

TREATMENT PLANNING AND ABERRATION CORRECTION ALGORITHMS FOR HIGH INTENSITY FOCUSED ULTRASOUND (HIFU) ABLATION OF SOFT TISSUE TARGETS

CROSS-REFERENCE TO RELATED APPLICATION

This application claims the benefit of U.S. Provisional Application No. 63/681,309, filed Aug. 9, 2024, the entire disclosure of which is hereby incorporated by reference in its entirety for all purposes

STATEMENT OF GOVERNMENT LICENSE RIGHTS

This invention was made with government support under Grant Nos. R01EB007643 and R01GM122859, awarded by the National Institutes of Health. The government has certain rights in the invention.

BACKGROUND

Non-invasive ultrasound surgery is a rapidly evolving technology that allows thermal or mechanical ablation of pathological tissues using continuous or pulsed high-intensity focused ultrasound (HIFU) exposures, respectively. While HIFU methods have demonstrated remarkable success in various clinical applications, critical challenges caused by beam aberrations have been revealed when treating deep abdominal tumors of the HIFU beam caused by intervening tissues. Such aberrations arise from phase shifts that vary across the HIFU wavefront due to the differences in thickness, sound speed, and density of tissue layers along the corresponding acoustic paths. Aberrations can lead to a substantial decrease in HIFU intensity at the focus, spatial shift and broadening of the focal lobe, and formation of secondary lobes outside the target region. These effects may compromise the safety and efficacy of HIFU ablation. Among other soft tissues, fat introduces the most severe aberrations due to the lowest sound speed, which substantially differs from water-based tissues. Additionally, adipose tissues have very high attenuation and the lowest cavitation threshold. During transcutaneous sonication of deep abdominal targets, significant phase aberrations can occur, primarily due to spatially inhomogeneous distribution of subcutaneous and visceral fat. Arguably the worst case of beam aberration is encountered in HIFU ablation of renal tumors due to the presence of perirenal fat.

Accordingly, systems and methods for improved accuracy of HIFU treatments are still needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Briefly, the inventive technology is directed to high-intensity focused ultrasound (HIFU) applications for thermal or mechanical ablation of tumors (e.g., renal tumors). Such HIFU applications often encounter challenges due to significant beam aberration and refraction caused by oblique beam incidence, inhomogeneous tissue layers, and presence of gas and bones within the path of the beam. With embodiment of the inventive technology, these distortions of the beam can be significantly mitigated through sonication geometry planning, patient positioning, and aberration correction using multi-element phased arrays. In some embodiments, a sonication planning algorithm is introduced based on simulations that select the optimal transducer position, evaluate the effect of aberrations and acoustic field quality at the target region after aberration correction. Optimization of transducer positioning may be implemented using a graphical user interface (GUI) to visualize a segmented 3D computed tomography (CT)-based acoustic model of the body and to select sonication geometry through a combination of manual and automated approaches. After array positioning, the correction of aberrations can be performed using a combination of backpropagation from the focus with a numerical optimization (e.g., an ordinary least squares (OLS) optimization) of phases at the array elements. In some embodiments, the forward propagation is simulated using a combination of the Rayleigh integral and k-space pseudospectral method (k-Wave toolbox). After correction, simulated HIFU field is characterized by tight focusing and up to 3-fold higher maximum pressure within the target region in comparison to the conventional ray tracing methods. In some embodiments, the addition of numerical optimization to the aberration correction method yielded up to 30% higher maximum pressure compared to the conventional diffraction-based backpropagation to the centers of the array elements. The inventive technology may be particularly useful in strongly distorted cases.

In one embodiment, a method for planning a sonication treatment of a target in a body includes obtaining a 3D anatomical model of the target and a portion of the body that is disposed between an ultrasound transducer and the target, where the ultrasound transducer is a phased array ultrasound transducer comprising a plurality of elements. The method also includes selecting a position of the ultrasound transducer by applying a transducer positioning algorithm for optimizing a sonication geometry. The method also includes simulating an aberrated ultrasound field at the target, where the aberrated ultrasound field is a linear high-intensity focused ultrasound (HIFU) field; and compensating for phase aberrations of the aberrated ultrasound field by back-propagating an ultrasound field from a virtual point source at the target, through the portion of the body that is disposed between the ultrasound transducer and the target, toward the ultrasound transducer, wherein the ultrasound field is spherical at the virtual point. Based on backpropagating the ultrasound field from the virtual point, time delays are determined at the elements of the ultrasound transducer, where the time delays are configured for compensating the phase aberrations of the ultrasound field at the virtual point source.

In one aspect, a first location of an initial target at the virtual point source at the target is different from a second location of a final target obtained with the time delays at the elements of the ultrasound transducer.

In one aspect, time delays are configured for generating a maximum pressure field at the final target.

In another aspect, the time delays of each element are configured based on a non-uniform phase distribution over each element.

In one aspect, the transducer positioning algorithm includes: setting an orientation of the ultrasound transducer to avoid gas and to minimize a volume percentage of bones inside a focusing cone; determining a parameter space within which a volume percentage of gas and the volume percentage of bones are approximately the same; adjusting the orientation of the ultrasound transducer to minimize a surface area percentage of bones; adjusting the orientation of the ultrasound transducer within a narrowed parameter space to minimize a volume percentage of fat inside the focusing cone; adjusting the orientation of the ultrasound transducer within the narrowed parameter space to minimize distortion of an intersection contour; and within the narrowed parameter space, automatically finding a local minimum of an angle between an array axis and a normal to a skin surface.

In one aspect, the transducer positioning algorithm is configured for minimizing interference with bones and fat tissue along a beam path; and achieving a normal incidence of an ultrasound beam on the skin surface.

In one aspect, compensating for the phase aberrations is based on an ordinary least squares (OLS) optimization of phases at the elements of the ultrasound transducer.

In one aspect, the method also includes applying a high-intensity focused ultrasound (HIFU) by the ultrasound transducer, where the elements of the ultrasound transducer are activated in accordance to the time delays.

In one aspect, the method includes setting boundary conditions for simulating the aberrated ultrasound field at the target.

In one aspect, the method also includes selecting a shape and a size of the ultrasound transducer.

In one aspect, the 3D anatomical model is obtained by: a computed tomography (CT); a magnetic resonance imaging (MRI); or a three-dimensional (3D) ultrasound visualization.

In one aspect, the target is separated by soft tissue from the ultrasound transducer. In one aspect, the target is: a prostate; a liver; a kidney; a pancreas, or a breast of a patient.

In one aspect, the target is located within an abdominal area of the body.

In one embodiment, a system for sonication planning of a target in a body includes: a phased array ultrasound transducer comprising a plurality of elements, each element being configured for emitting ultrasound at a selected phase. The system also include a controller configured for: obtaining a 3D anatomical model of the target and a portion of the body that is disposed between the ultrasound transducer and the target; selecting a position of the ultrasound transducer by applying a transducer positioning algorithm for optimizing a sonication geometry; and simulating an aberrated ultrasound field at the target, where the aberrated ultrasound field is a linear high-intensity focused ultrasound (HIFU) field. The controller is also configured for compensating for phase aberrations of the aberrated ultrasound field by: backpropagating an ultrasound field from a virtual point source at the target, through the portion of the body that is disposed between the ultrasound transducer and the target, and toward the ultrasound transducer, where the ultrasound field is spherical at the virtual point; and based on backpropagating the ultrasound field from the virtual point, determining time delays at the elements of the ultrasound transducer, where the time delays are configured for compensating the phase aberrations of the ultrasound field at the virtual point source.

In one aspect, the controller is further configured for setting boundary conditions for simulating the aberrated ultrasound field at the target.

In another aspect, the controller is further configured for: minimizing interference of bones and fat tissue along a beam path; and achieving a normal incidence of an ultrasound beam on skin surface.

In one aspect, the controller is further configured for: setting an orientation of the transducer to avoid gas and to minimize a volume percentage of bones inside a focusing cone; determining a parameter space within which a percentage of gas and bones is approximately the same; adjusting the orientation of the transducer to minimize a surface area percentage of bones; adjusting the orientation of the transducer within a narrowed parameter space to minimize a volume percentage of fat inside the focusing cone; adjusting the orientation of the transducer within the narrowed parameter space to minimize distortion of an intersection contour; and within the narrowed parameter space, automatically finding a local minimum of an angle between an array axis and a normal to the skin surface.

In one aspect, the controller is further configured for determining the time delays of each element based on a non-uniform phase distribution over each element.

In one aspect, the compensating for the phase aberrations is based on an ordinary least squares (OLS) optimization of phases at the elements of the ultrasound transducer.

In one aspect, the target is obstructed by a layer of fat tissue.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings, where.

DETAILED DESCRIPTION

Figure 1:
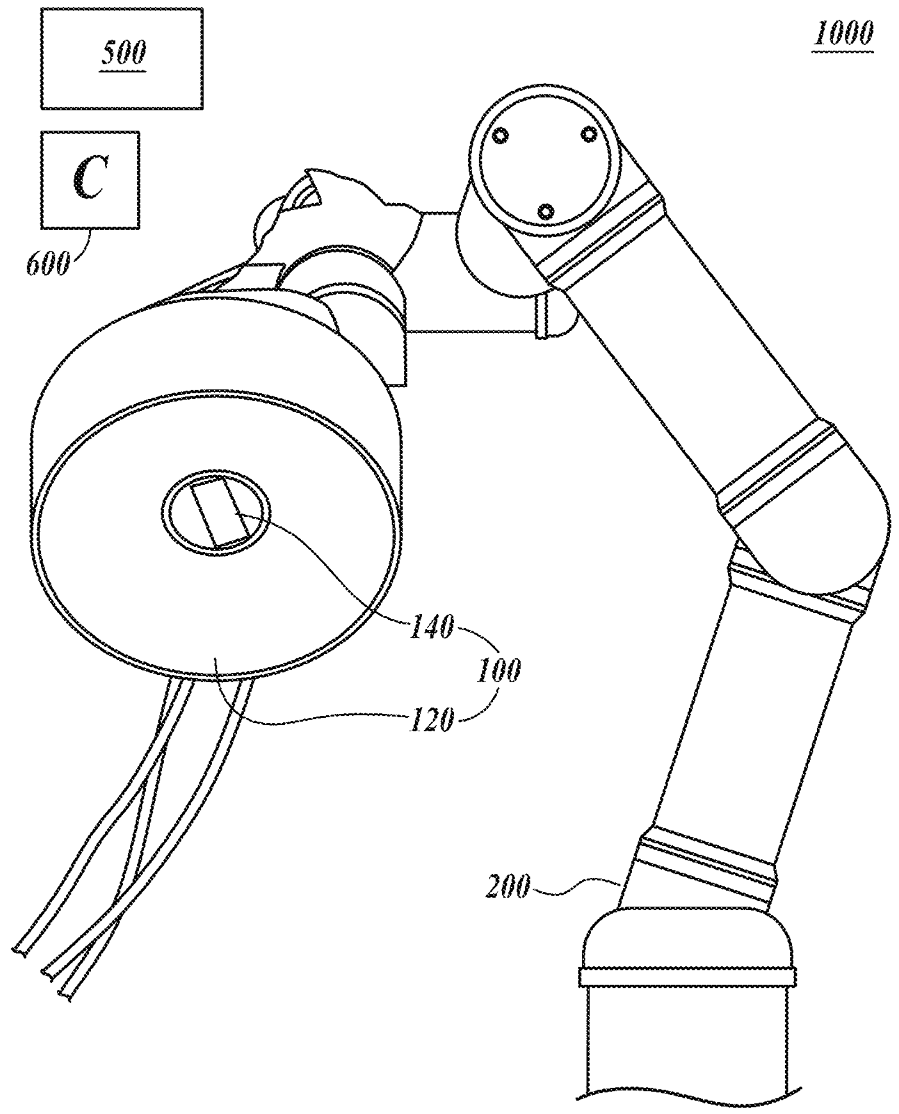
FIG. 1 is a schematic diagram of an ultrasound system in accordance with an embodiment of the present technology.

While illustrative embodiments have been illustrated and described, it will be appreciated that various changes can be made therein without departing from the spirit and scope of the invention.

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those skilled in the art that variations may be applied to the articles and/or methods and in the steps or in the sequence of steps of the method described herein without departing from the concept, spirit, and scope of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" may mean "one", but it is also consistent with the meaning of "one or more", "at least one", and "one or more than one". The use of the term "or" is used to mean "and/or" unless explicitly indicated to refer to alternatives only if the alternatives are mutually exclusive, although the disclosure supports a definition that refers to only alternatives "and/or". Throughout this application, the term "about" is used to indicate that a value includes the inherent variation of error for the quantifying device, the method being employed to determine the value, or the variation that exists among the study subjects. For example, but not by way of limitation, when the term "about" is utilized, the designation value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

In the context of this disclosure, the terms "about," "approximately," "generally" and similar mean +/−5% of the stated value.

FIG. 1 is a schematic diagram of an ultrasound system 1000 in accordance with an embodiment of the present technology. The ultrasound system 1000 includes an ultrasound probe 100 having a therapy transducer 120 and an imaging transducer 140. The ultrasound probe 100 may be controlled by a controller (e.g., a computer) 600 having suitable software and commands for controlling the therapy transducer and imaging transducer. A monitor 500 can display images of the target tissue of the patient that are obtained, for example, by the imaging transducer of the ultrasound probe 100 or by a separate imaging device (e.g., a computational tomography (CT) system).

Figure 2:
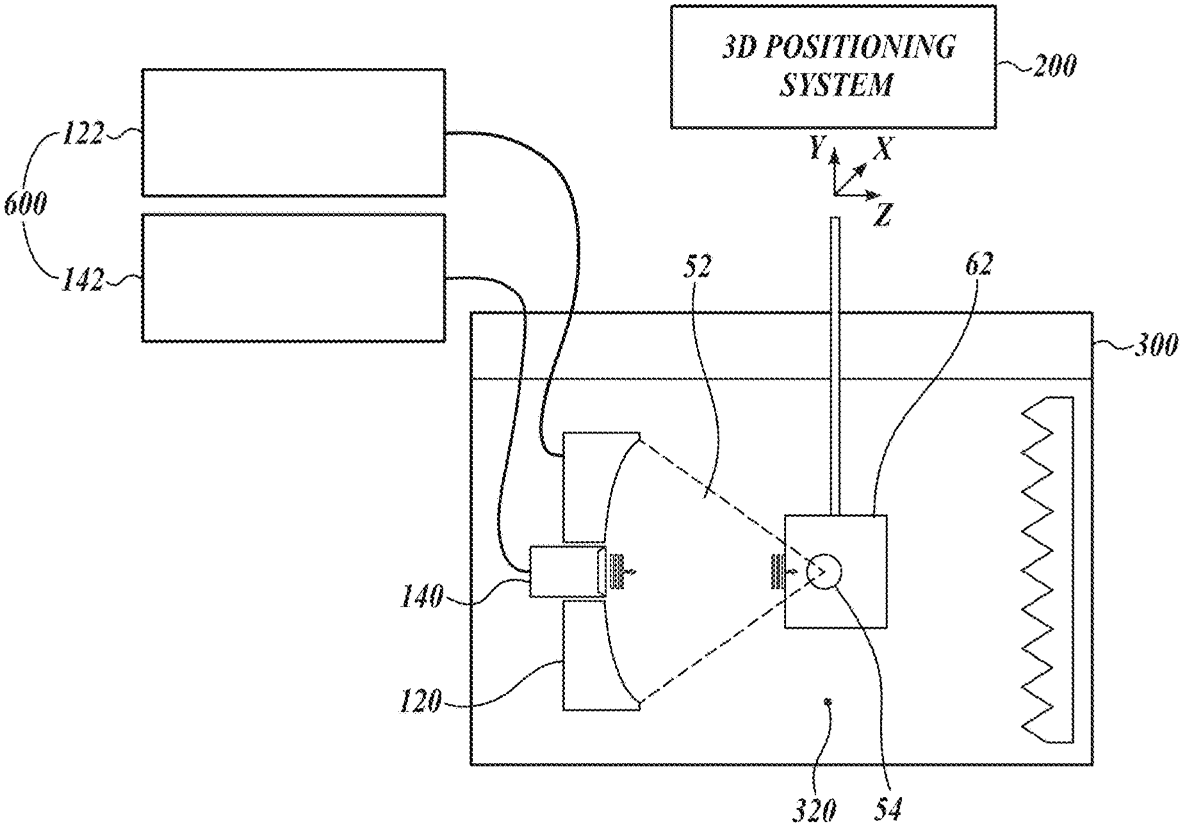
FIG. 2 is a schematic diagram of an ultrasound system in accordance with an embodiment of the present technology.

FIG. 2 is a schematic diagram of an ultrasound system for in accordance with an embodiment of the present technology. The illustrated HIFU system is a test setup using a test tissue 62. In some embodiments, a HIFU therapy transducer 120 is controlled by high power driving electronics 122. The therapy transducer 120 may be a phased array ultrasound transducer having multiple elements that operate with pre-determined phase delays. In some embodiments, an ultrasound imaging transducer 140 is mounted at the center opening of the HIFU therapy transducer 120, but other arrangements and locations of the ultrasound imaging transducer 140 are also possible. The imaging transducer 140 may be a phased array ultrasound transducer. In some embodiments, the imaging transducer 140 may be functionally replaced by a CT system or a magnetic resonance imaging (MRI) system. The driving electronics 122 and control electronics 142 may be collectively referred to as a controller for simplicity and brevity. In other embodiments, the driving electronics 122 and control electronics 142 may be parts of the controller 600. When the therapy transducer 120 and/or imaging transducer 140 are phased array transducers, the driving electronics 122 and control electronics 142 drive individual elements of the transducers with appropriate phase offset to generate a pre-determined pressure/amplitude field at the target area.

For testing purposes, the transducer assembly 120/140 may be mounted into a tank 300 filled with degassed, deionized water 320. The tissue sample 62 (e.g., representing a tissue of a hypothetical patient) is placed in front of the transducer in a holder attached to a 3D positioning system 200. A person of ordinary skill will understand that for testing purposes there is an equivalency between repositioning the test tissue with respect to the transducer assembly 120/140 and repositioning the transducer assembly 120/140 with respect to the test tissue. Dash lines 52 indicate focusing of the HIFU waves onto a focal area 54.

Figure 3A:
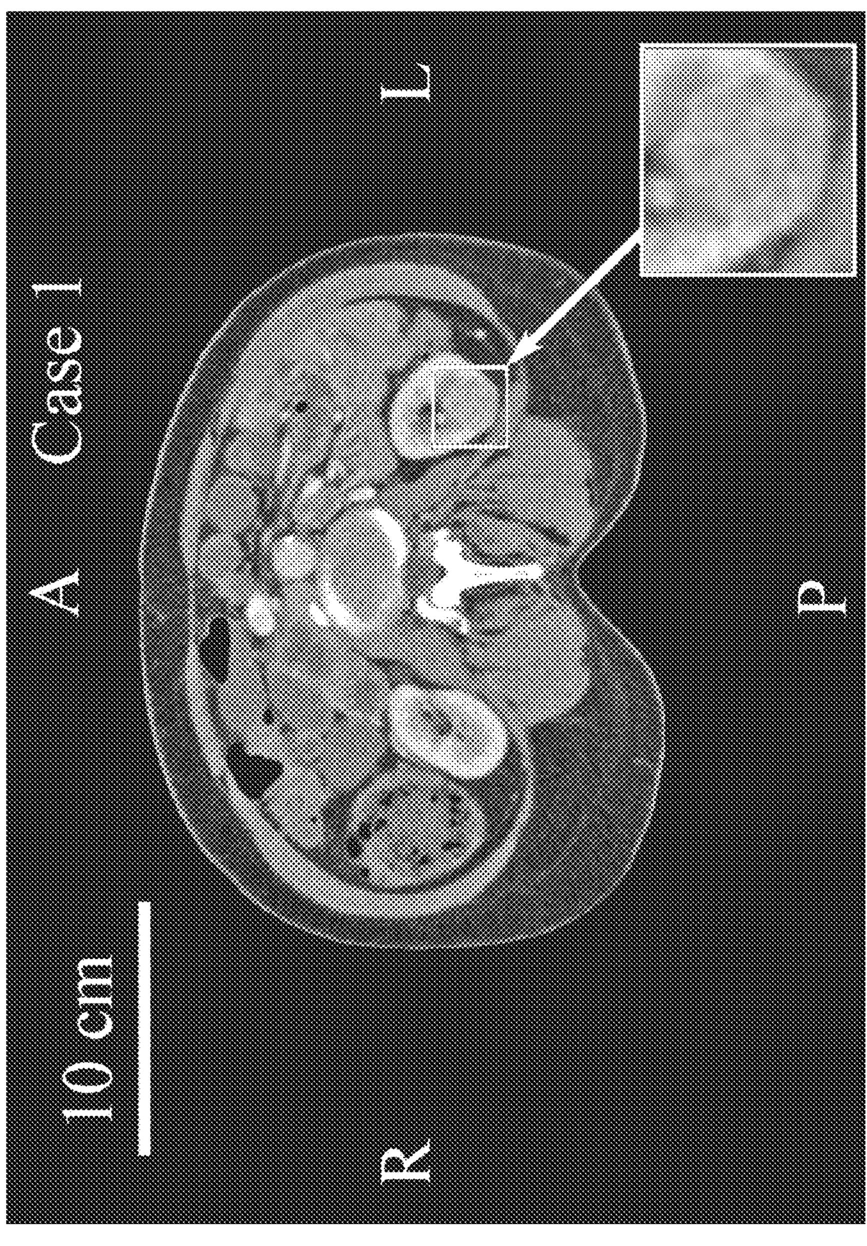
FIGS. 3A-3C are axial CT-scans in accordance with embodiments of the present technology.
Figure 3B:
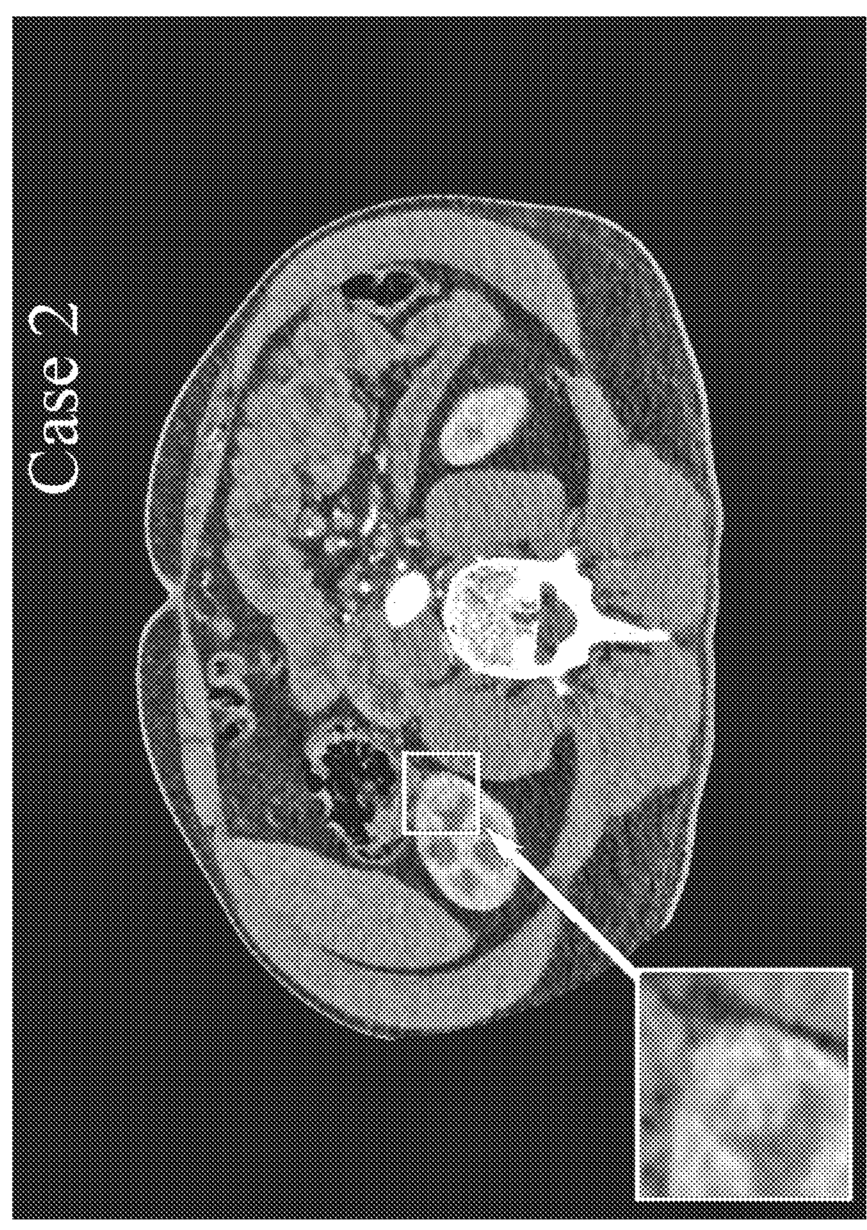
Figure 3C:
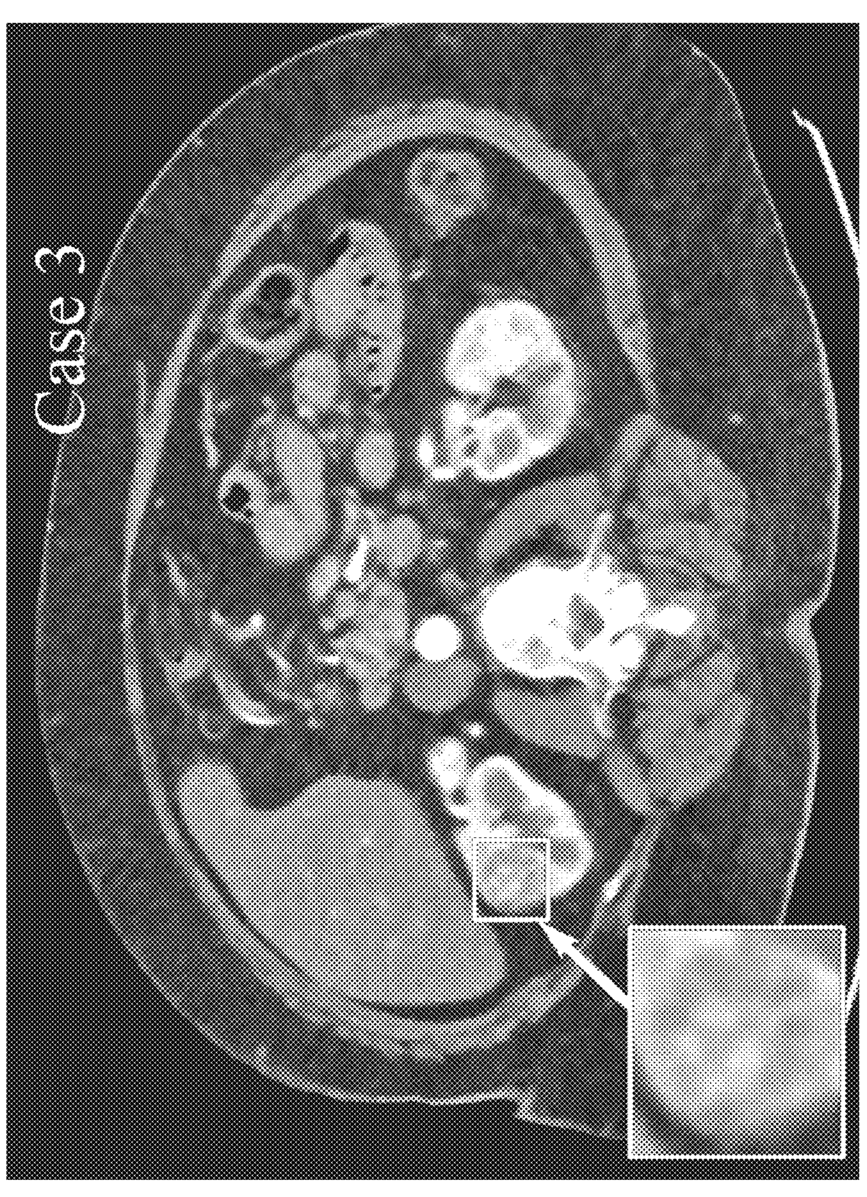

FIGS. 3A-3C are axial CT-scans in accordance with embodiments of the present technology. As explained above, the inventive technology may be understood as involving two steps. The first step is to develop a patient-specific procedure to determine an optimal positioning of the HIFU-source prior to sonication of a target (e.g., an abdominal target). The procedure may be implemented as a graphical user interface (GUI) software that visualizes a CT-based 3D acoustic model of a subject's anatomy and allows the user to combine manual and automated approaches to select the sonication geometry.

The second step is to develop a visualization-based (e.g., based on a CT imaging, a 3D-ultrasound imaging, etc.) aberration correction method that addresses the challenge of accurately reproducing the backpropagated wavefront through different segments of the tissue using a discrete distribution of array elements of the phased array ultrasound transducer. The backpropagation of the ultrasound wavefront takes into account differences in propagation speed and density for different types of tissues that the ultrasound wavefront propagate through on its path to the target focal area (e.g., a tumor). In some embodiments, the modified backpropagation method utilizes ordinary least squares (OLS) optimization of the phases at the array elements after backpropagation to achieve a smooth transition from a continuous distribution of phases across the wavefront over the surface of each element of the array to a discrete one. The optimized phases, when applied to the ultrasound transducer array elements, result in higher ultrasound pressures at the target area of the patient.

FIGS. 3A-3C illustrate a set of three cases of renal cell carcinoma (RCC) in subjects with different body habitus and tumor locations. In particular, axial CT-scans of renal cell carcinoma cases are shown. Magnified regions correspond to the tumors in each case. In the three cases shown in FIGS. 3A-3C, A, P, R, L represent the anterior, posterior, right, and left anatomical directions, respectively.

Three full body CT scans of FIGS. 3A-3C come from the patients with tumor locations and sizes (3-4 cm), which could be treated with HIFU, but with differing difficulties. All patient scans were performed on the same model CT scanner (Siemens Biograph 16, Germany), operating at 120 kV voltage to obtain the sets of 512×512 pixel axial images.

The dataset for FIG. 3A includes 152 axial images with a resolution of 0.74 mm×0.74 mm and a slice thickness of 3 mm. The tumor was located in the posterior lower pole of the left kidney providing a good acoustic window for HIFU-treatment through a window free of bones and gas-filled hollow abdominal viscera.

The dataset for FIG. 3B includes 384 axial slices, 0.71 mm×0.71 mm resolution, and 0.63 mm slice thickness. The tumor was located on the anteromedial lower pole of the right kidney (FIG. 1*b*) and was partially blocked by the right iliac bone, making the acoustic window more challenging.

The dataset for FIG. 3C includes 358 axial images, 0.98 mm×0.98 mm resolution, and 0.63 mm slice thickness. The tumor was located in the anterior upper pole of the right kidney (FIG. 1*c*) in an obese patient. As a result, the tumor was at significant depth with a thick (up to 7 cm) fat layer within the acoustic path, which is well known to be strongly attenuative for ultrasound. In addition to the strongly attenuative adipose tissue, the 11th and 12th ribs partially covered the beam path to the tumor.

The sample HIFU system used in implementing the algorithm was a 1.5 MHz HIFU array comprising 256 circular elements arranged in the spiral pattern, but in different embodiments other arrangements of the elements of the phase array ultrasound transducer can be used. The example phased array may be employed in transabdominal pre-clinical studies on boiling histotripsy of kidney and liver and acoustic manipulation as well as manipulating kidney stones in vivo through abdominal wall in a porcine model. In other embodiments, the target may be a prostate, a liver, a pancreas, or a breast of the patient. In some embodiments, the target is located within an abdominal area of the body.

The "backpropagation+OLS" correction method may be applied to the same set of three RCC patient acoustic models to evaluate the degree of phase aberration and achievable improvements with correction, under selected sonication geometry, as further described below.

Figure 4B:
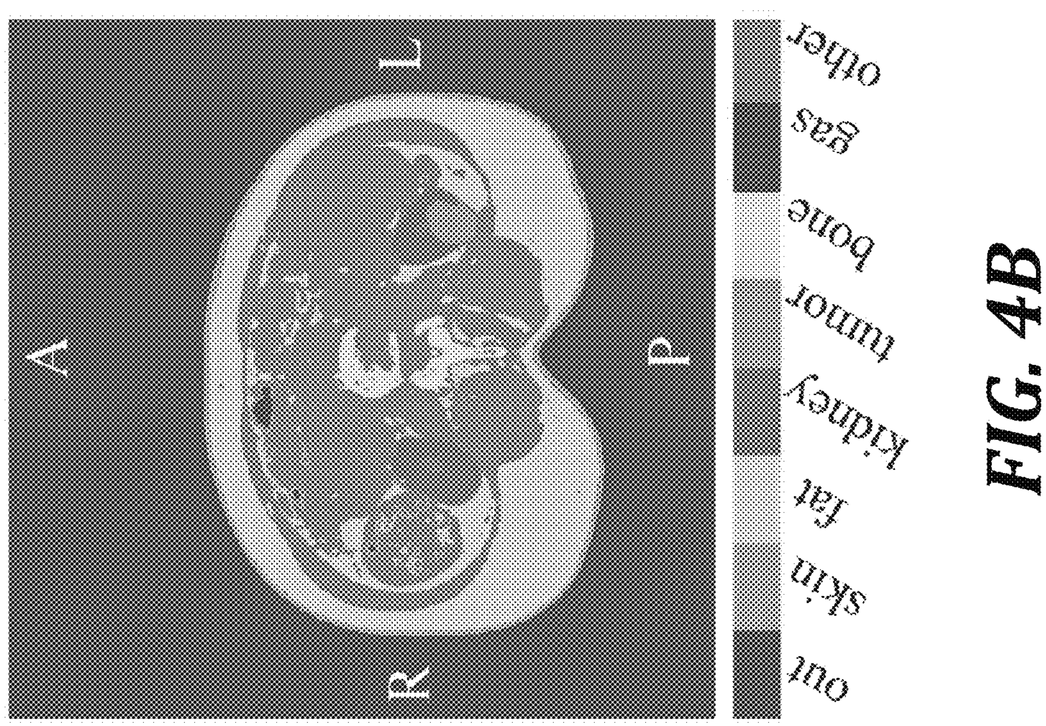
FIGS. 4A-4B are graphs reconstructed from radiodensity distributions representing density and sound speed (A) and distributions of tissue types (B) within a segmented slice of a target tissue in accordance with an embodiment of the present technology.
Figure 4A:
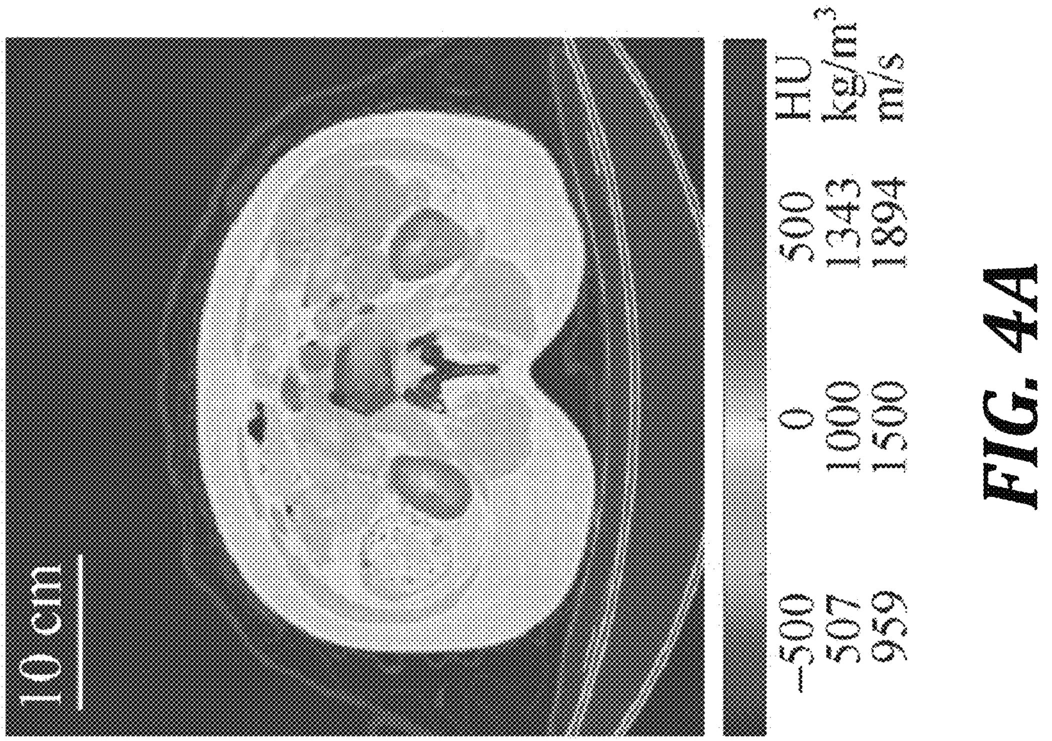

FIGS. 4A-4B are graphs obtained from radiodensity distributions within a segmented slice of a target tissue in accordance with an embodiment of the present technology. 3D CT data, expressed in Hounsfield units (HU), were resampled using linear interpolation to give a resolution of 0.3 mm×0.3 mm×0.3 mm suitable for simulations. This spatial grid step is less than $\lambda_w/3$, and has been shown to be sufficient for pseudospectral k-Wave calculations. Here, $\lambda_w=2\pi f_0/c_w$ is the wavelength, $f_0=1.5$ MHz is the operating frequency of the HIFU-array, and $c_w=1540$ m/s is the average sound speed in soft tissues.

The density and sound speed distributions (FIG. 4A) were calculated from HU using appropriate conversion equations. Since acoustic attenuation does not correlate with HU, it was assigned to specific tissue types segmented using an open-source software package "3D Slicer" which is available in public domain. The segmented tissues were classified into eight types: space filled with coupling water ("out"), skin, fat, kidneys, tumor, bones, gas, and other (FIG. 4B). For simplicity, the "other" tissue type, representing all other water-based abdominal tissues and muscle, was assigned the same acoustic properties as skeletal muscle. The ultrasound attenuation coefficient $\alpha$ was considered homogeneously distributed within each tissue type and assigned the following literature values: 0 Np/m for "out", 31.7 Np/m for "skin", 6.77 Np/m for "fat", 4.25 Np/m for "kidneys" and "tumor", 76.5 Np/m for "bones", 346 Np/m for "gas", and 11 Np/m for "other." However, a person of ordinary skill would know that other numbers and types of tissue classification are also possible in different embodiments. For reference, the sound speed and density calculated from HU for the most aberrative segments on the beam path and averaged across all cases were (mean±standard deviation): 1448±39 m/s and 944±35 kg/m$^3$ for "fat"; and 1545±59 m/s and 1031±52 kg/m$^3$ for "other".

Figure 5:
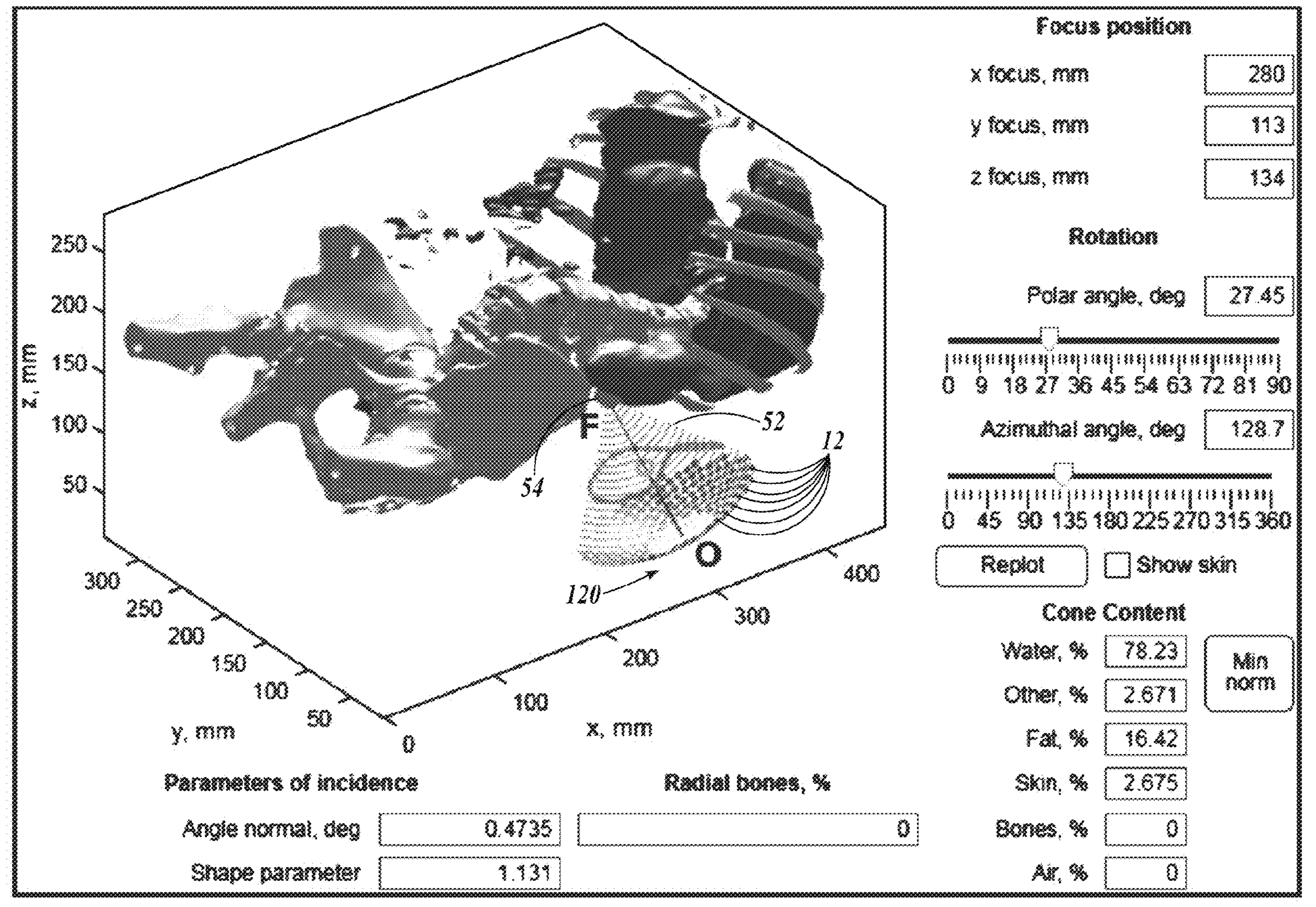
FIG. 5 illustrates a main window of the sonication planning graphical user interface (GUI) in accordance with an embodiment of the present technology.

FIG. 5 illustrates a main window of the sonication planning graphical user interface (GUI) in accordance with an embodiment of the present technology. In particular, FIG. 5 is related to the above FIG. 3A. The example positioning algorithm may be implemented with a MATLAB graphical user interface (GUI) application. The parameters of the transducer and the 3D segmented tissue model may be preloaded from the corresponding MATLAB data files, which contain geometric parameters of the source and polygon data for surfaces of the abovementioned tissue segments. In some embodiments, the ultrasound transducer 120 having a 1.5 MHz multi-element array (aperture D=144 mm, radius of curvature F=120 mm, and radius of the elements 12 being a=3.5 mm) with a compact spiral layout of N=256 circular elements was used. The GUI plots the surfaces of the tissue types relevant to optimization of transducer positioning, e.g., kidneys, tumor, bones, and gas. The GUI displays the HIFU array in a position specified by the user. Orientation of the transducer relative to the anatomic model is defined via GUI using five parameters: x, y, and z coordinates of the focal point 54, polar, and azimuthal angles. Here the polar angle φ is the angle between the inverted z-axis direction and the vector FO; the azimuthal angle θ is the angle between the x-axis direction and the orthogonal projection of the vector FO on the xy-plane. Once the user changes the polar or azimuthal angle, the transducer 3D model is redrawn in real time in the plot. At the same time, quantitative parameters of the acoustic path of the ultrasound field 52 in the current transducer position are displayed in textboxes under "Cone Content." Those parameters provide a percentage of the volume (% vol.) of different tissues within the cone formed by rays connecting the transducer edges to the focal point 54 ("the focusing cone"). Another parameter "Radial bones" shows the maximum surface area percentage (% surf.) of "bones" among all cross-sections of the focusing cone volume.

Normal incidence of the HIFU beam onto the skin surface may be important for maintaining tight focusing, as oblique incidence leads to reflections and refraction and thus to relocation and degrading of the focus. To address this issue, the program allows the user to estimate the parameters that characterize the normal incidence of the beam. "Angle normal" provides the angle γ between the HIFU array axis and the normal to the skin surface. The intersection point is plotted as a circle marker. Finally, the "Shape parameter" is another quantitative descriptor of the beam incidence angle. It estimates the distortion level of the contour of intersection of the focusing cone and the skin surface (thick solid line in FIG. 5). The shape parameter was determined as $\sigma=L^2/4\pi S$, where L is the perimeter of the contour of intersection and S is its area. For example, σ=1 for a circular intersection contour, and stronger distortion of the circular contour correspond to greater values of σ.

Using the sample GUI, the position of the HIFU array described by the two angles—φ and θ—may be optimized for each case with the following procedure. In some embodiments, all the procedure steps except the last one were manual. In some embodiments, the procedure is as follows:

- Set a starting orientation of the transducer to avoid gas and to provide minimum possible volume percentage of bones inside the focusing cone ("Cone content" in FIG. 5).
- Determine the parameter space Φ0 for φ and θ within which the percentage of gas and bones is approximately the same.
- Adjust the starting orientation within the above-mentioned parameter space Φ0 to minimize surface area percentage of bones ("Radial bones"). Note that this narrows the parameter space from Φ0 to Φ1 or (Φ0→Φ1).
- Adjust the orientation within narrowed parameter space Φ1→Φ2 to minimize the volume percentage of fat in the focusing cone ("Cone content", "Fat").
- Adjust the orientation within narrowed parameter space Φ2→Φ3 to minimize distortion of the intersection contour described by σ (per "Shape parameter").
- Within the narrowed parameter space Φ3 automatically find a local minimum of the angle γ between the array axis and normal to the skin surface. The minimization problem for a two-dimensional function γ(φ,θ) can be solved numerically by the Nelder-Mead method. The "Min norm" button launches the solver of minimization problem in the GUI.

Figure 6A:
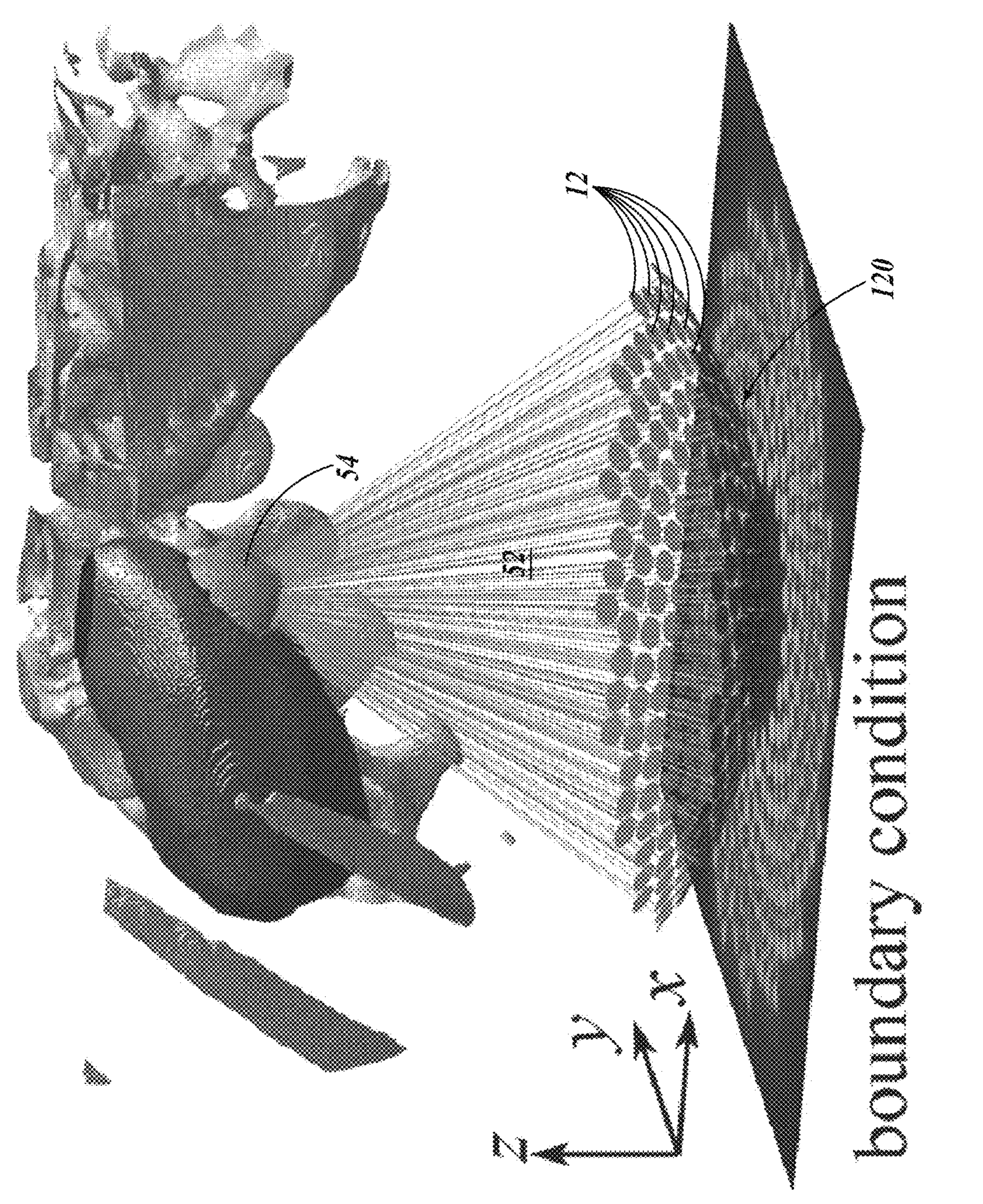
FIGS. 6A-6C illustrate different HIFU field modelling steps in accordance with embodiments of the present technology.
Figure 6B:
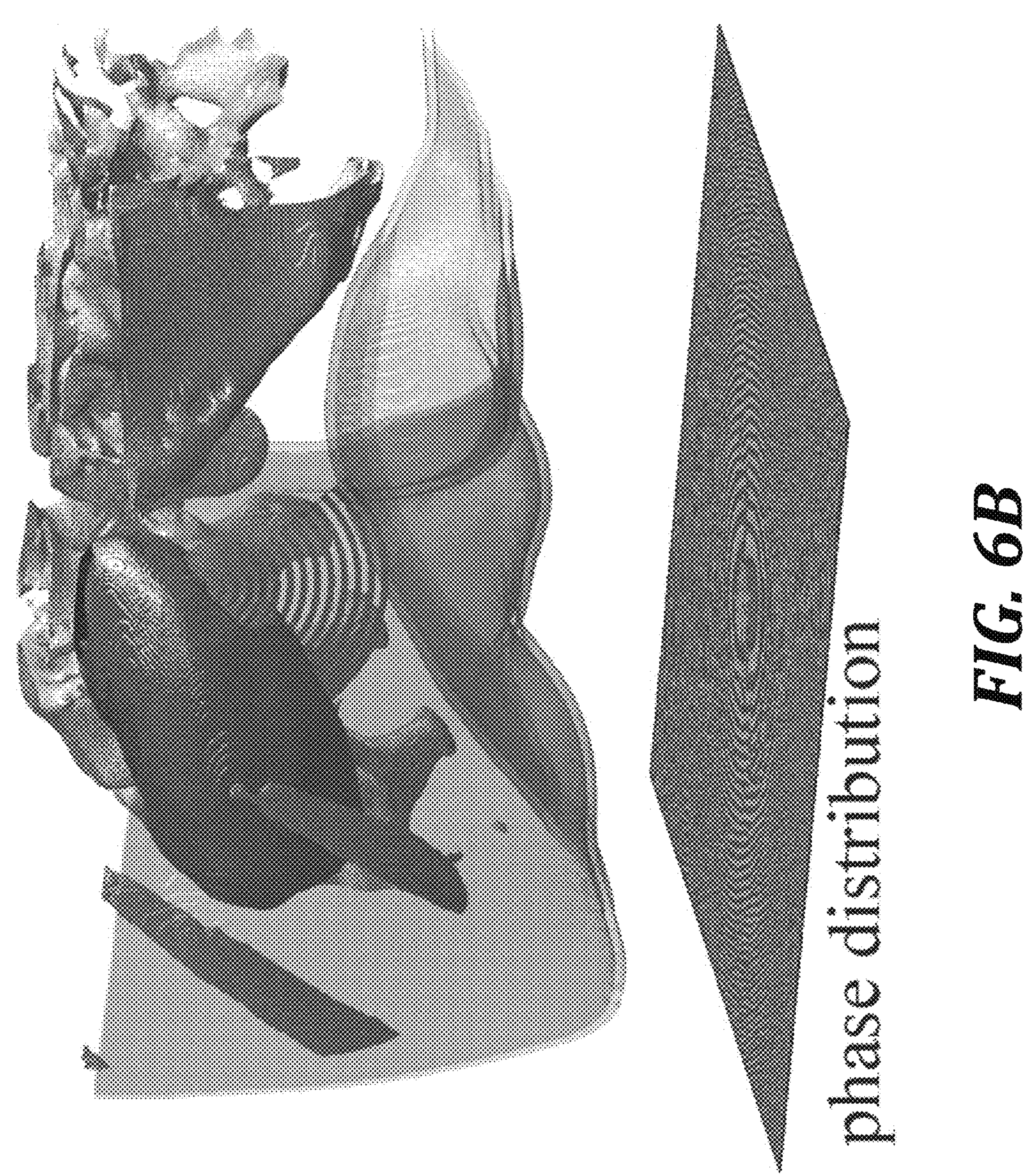
Figure 6C:
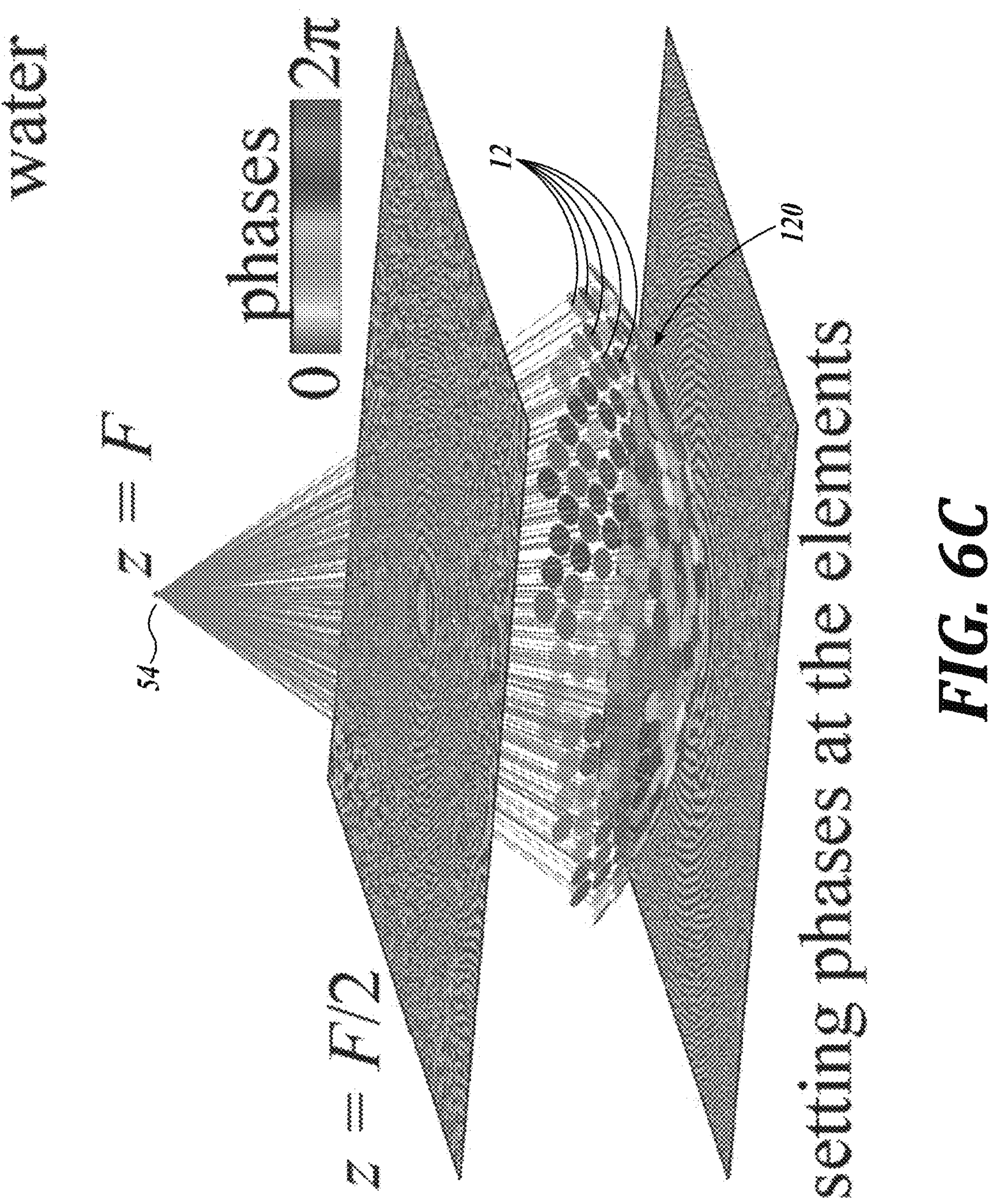

FIGS. 6A-6C illustrate different HIFU field modelling steps in accordance with embodiments of the present technology. The wave propagation through the acoustic models described above is simulated using a system of coupled first-order partial differential equations of linear acoustics:

$$\begin{cases} \frac{\partial u}{\partial t} = -\frac{1}{\rho_0}\nabla p, \\ \frac{\partial \rho}{\partial t} = -\rho_0\nabla u - u\nabla\rho_0 + M, \\ p = c_0^2\left(\rho + d\nabla\rho_0 + 2\alpha_0 c_0\frac{\partial \rho}{\partial t}\right). \end{cases} \quad (1)$$

Here p is the acoustic pressure, u is the particle velocity, d is the particle displacement, ρ is the acoustic density, t—time. The acoustic properties of the propagation medium are assumed to vary in space and can be denoted as functions of the position vector r: $\rho_0(r)$ is the density, $c_0(r)$ is the sound speed, $\alpha_0(r)$ □ is the pre-factor for the absorption coefficient $$\alpha = 4\pi^2\alpha_0 f_0^2.$$

The HIFU source here is described by a mass source term M(r,t) that represents the temporal rate of the input of mass per unit volume.

Simulations may be implemented using the open-source k-Wave MATLAB Toolbox that utilizes k-space pseudospectral method for acoustic wave propagation in heterogeneous medium, but other simulation tools may also be used. In the illustrated example, the following simulation parameters were selected: R×R×D points in the x, y, and z directions (FIG. 6A), where R=648, D=512. The spacing between grid points of Δx=Δy=Δz=h=0.3 mm (voxel volume $\Delta v=h^3=0.027\ mm^3$) was selected. A perfectly matched layer (PML) occupied 10 points around each edge of the spatial domain, and the time step was based on the Courant-Friedrichs-Lewy (CFL) number of 0.3. Here $CFL=c_{max}\Delta t/\Delta x$ and $c_{max}$ is the maximum sound speed in the propagation medium.

The boundary condition to the Eq. (1) is set in the apex plane of the array with an additional calculation since the array elements are distributed not in the plane, but over a spherical surface. The boundary condition is first set at the surface of the array elements assuming uniform vibration at the operating frequency $f_0$. Next, the Rayleigh integral is used to backpropagate the field from the spherical surface of the array to the apex plane, z=0, located in coupling water as a part of the computational grid (FIG. 6A, "boundary condition"). Stated differently, this step includes backpropagating an ultrasound field from a virtual point source at the target toward the ultrasound transducer, where the ultrasound field is spherical at the virtual point. This procedure ensures a smooth and precise transfer of the boundary condition, which can be defined at the apex plane as follows:

$$U_n(x, y, z=0, t) = A_n(x, y)\sin[2\pi f_0 t + \varphi(x, y)]. \quad (2)$$

Here, $A_n(x,y)$ and $\varphi(x,y)$ are the amplitude and phase of the normal component of the vibrational velocity in the plane z=0. The mass source M(x,y,t) can be related to the boundary condition $U_n(x,y,t)$ in water with density $\rho_w$, by interpreting $U_n(x,y,t)$ as an injection of mass into each grid voxel at the apex plane. Then, the added mass at each voxel of the grid can be calculated as $\Delta m=2\rho_w \cdot U_n \Delta t \cdot h^2$ and $$M(x, y, t) = \frac{\Delta m}{\Delta t \Delta V} = \frac{2\rho_w U_n(x, y, t)}{h}. \tag{3}$$

In some embodiments, the k-Wave toolbox uses a scaled input matrix called source.p to define mass sources. In the illustrated case of a 3D simulation with the source located in water and the same grid step h along each spatial coordinate, the input matrix source.p is expressed as $0.5c_w hM$. Substituting equation (3) into expression above, source.

$$p = \rho_w c_w U_n^{ijs},$$

where $$U_n^{ijs} = U_n(x_i, y_j, t_s)$$

and subscripts i=1 . . . R and j=1 . . . R represent the i-th and j-th grid nodes in x and y directions, and s represents the time grid nodes.

In some embodiments, simulations of the forward propagation are first performed within the acoustic models via k-Wave as described above. Then, a virtual mass point source $M_F(t)=\sin(2\pi f_0 t)$ is placed at the target point inside the tumor. Two target points for each tumor case are considered: one at the pressure maximum of the distorted HIFU beam and the other one—at the center of curvature of the array. The linear acoustic field of the point source is calculated within the acoustic models, also via k-Wave, and the complex acoustic pressure amplitude $P_{back}(x,y,z=0)$ was obtained at the apex plane (FIG. 6B, "phase distribution") z=0 to prevent errors arising from the alignment of the spherical array surface and the Cartesian simulation grid. Then, two aberration correction methods are employed, both based on the "virtual source" technique.

The first algorithm may be understood as being equivalent to the "conventional backpropagation" algorithm commonly used in various studies of transcranial focusing. However, in the illustrated case, the Rayleigh integral was utilized to propagate the distribution $P_{back}(x,y,z=0)$ from the apex plane (z=0) to the active surface of the array, resulting in the vibrational velocity distribution at the array elements.

Figures 7A, 7B, 7C:
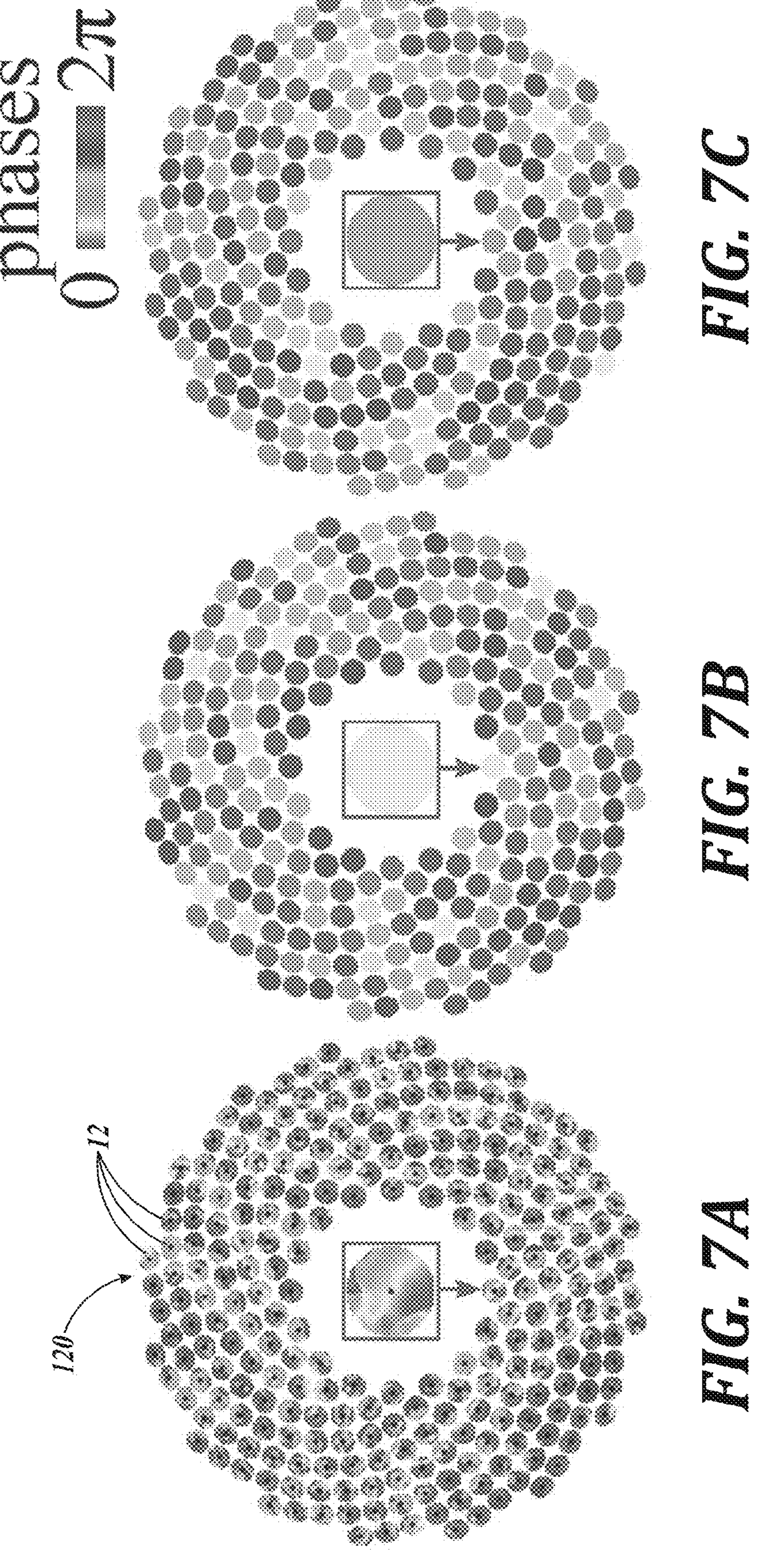
FIGS. 7A-7C illustrate phase distribution at the surfaces of the array elements in accordance with embodiments of the present technology.

FIGS. 7A-7C illustrate phase distribution at the surfaces of the array elements in accordance with embodiments of the present technology. An example of the resulting vibrational velocity phase distribution at the elements of the array is shown in FIG. 7A. As illustrated, the phase distribution over each element may be nonuniform (see the zoomed region in the middle representing a sample element 12). Conventional backpropagation methods set phases at the elements equal to the values at their centers and assume uniform phase distribution over each element (FIG. 7B). The obtained phases are then inverted and the resulting phases $$\varphi_l^{back}, l = 1 \ldots N,$$

are used to backpropagate the field to the apex plane to use for corrected HIFU field simulation.

The second algorithm modified the conventional technique described above by adding a numerical optimization procedure to set the correction phases at the array elements. Instead of using phase values at the element centers, as with the conventional technology, the phases of each element were calculated to best approximate the HIFU field that would be generated in the apex plane with non-uniform phase distribution over each element. Specifically, the complex amplitudes «, of the vibrational velocity at the array elements are determined that reproduces the complex amplitude matrix $P_{back}(x_i,y_j,z=0)$, which is obtained after initial backpropagation from the virtual source. In some embodiments, the algorithm includes the following steps.

The first step was to shift $P_{back}(x,y,z=0)$ forward, beyond the near field distance of a single element of the array, in current implementation—to half the array focal length $P_{F/2}(x,y,z=F/2)$. For this, the entire medium was replaced with water, and $P_{back}(x,y,z=0)$ was propagated forward using the Rayleigh integral.

Because the transferred distribution $P_{F/2}$ is located in the far field of each element, it could be expressed as a weighted sum of the analytical solutions for the far field of each element in water. Therefore, the optimization procedure of finding the complex amplitudes $\kappa_i$ at the elements that reproduce $P_{F/2}$ can be formulated as a set of linear matrix equations:

$$P_{F/2}^r = \sum_{l=1}^{N} C_{rl}\kappa_l, r = 1 \ldots R^2, l = 1 \ldots N. \tag{4}$$

Here $$P_{F/2}^r,$$

is the R×R matrix of complex pressure amplitudes $P_{F/2}(x_i, y_j, z=F/2)$ at the nodes of the spatial grid, reshaped as an $R^2 \times 1$ vector. The coefficients $C_{rl}$ depend on the spatial position of the node in the distribution $$P_{F/2}^r$$

(indexed as r) and the position of the element (indexed as l). The derivation of those coefficients for the far-field of a circular piston source can be found in available literature.

The next step involves solving the set of matrix equations (4). In the illustrated example, this set is overdetermined: the number of unknowns is N=256 and the number of equations is $R^2>10^5$, therefore, only approximate solution can be found. The method of ordinary least squares (OLS) gives a solution for the unknown complex amplitudes «, as a minimum of the function $\|\hat{C}\hat{\kappa}-\hat{P}_{F/2}\|^2$. Here, the ticks above variables denote the matrix $\hat{C} \equiv C_{rl}$ and the vectors $\hat{\kappa} \equiv \kappa_l$, $$\hat{P}_{F/2} \equiv P^r_{F/2}, \|\cdot\|^2$$

is the standard $L^2$ norm.

Finally, the OLS solution vector $\kappa_i$ was used to set phases at the elements, which were taken with a conjugated phase $$\varphi_l^{OLS} = -\arg(\kappa_l)$$

(FIG. 6C). At the same time, the amplitudes at the elements are equalized to maximize the power output of the array, since the wavefront shape is primarily determined by the phases.

The obtained phases at each element for Case 2 are shown in FIG. 7C, which noticeably differ from the ones obtained using conventional backpropagation in FIG. 7B. Thus, the modified method accounts for the condition of non-uniform vibration of each element and does not use the approximations of the phase by its value at the element center.

Figure 8A:
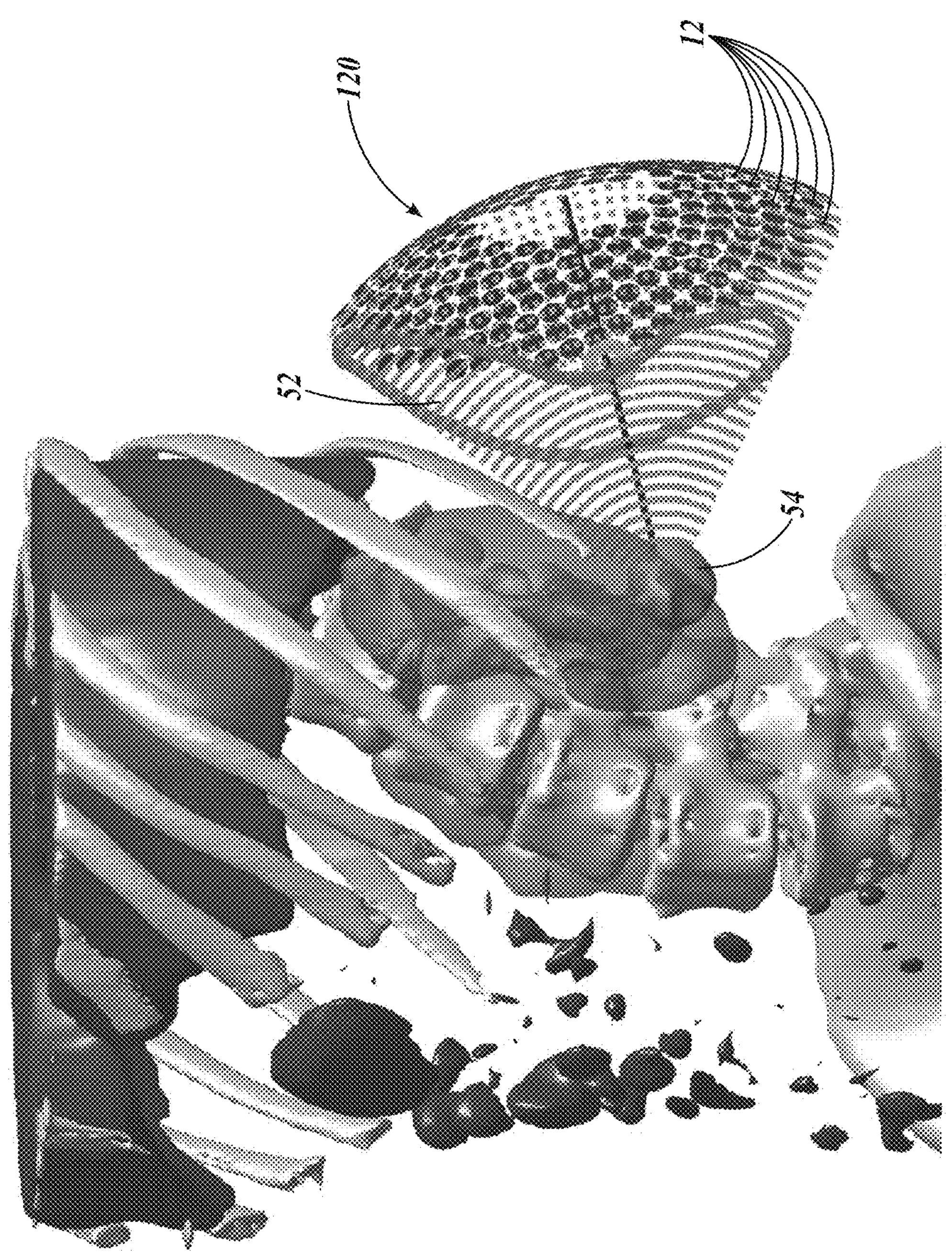
FIGS. 8A-8C illustrate optimized sonication geometries for test cases in accordance with an embodiment of the present technology.
Figure 8B:
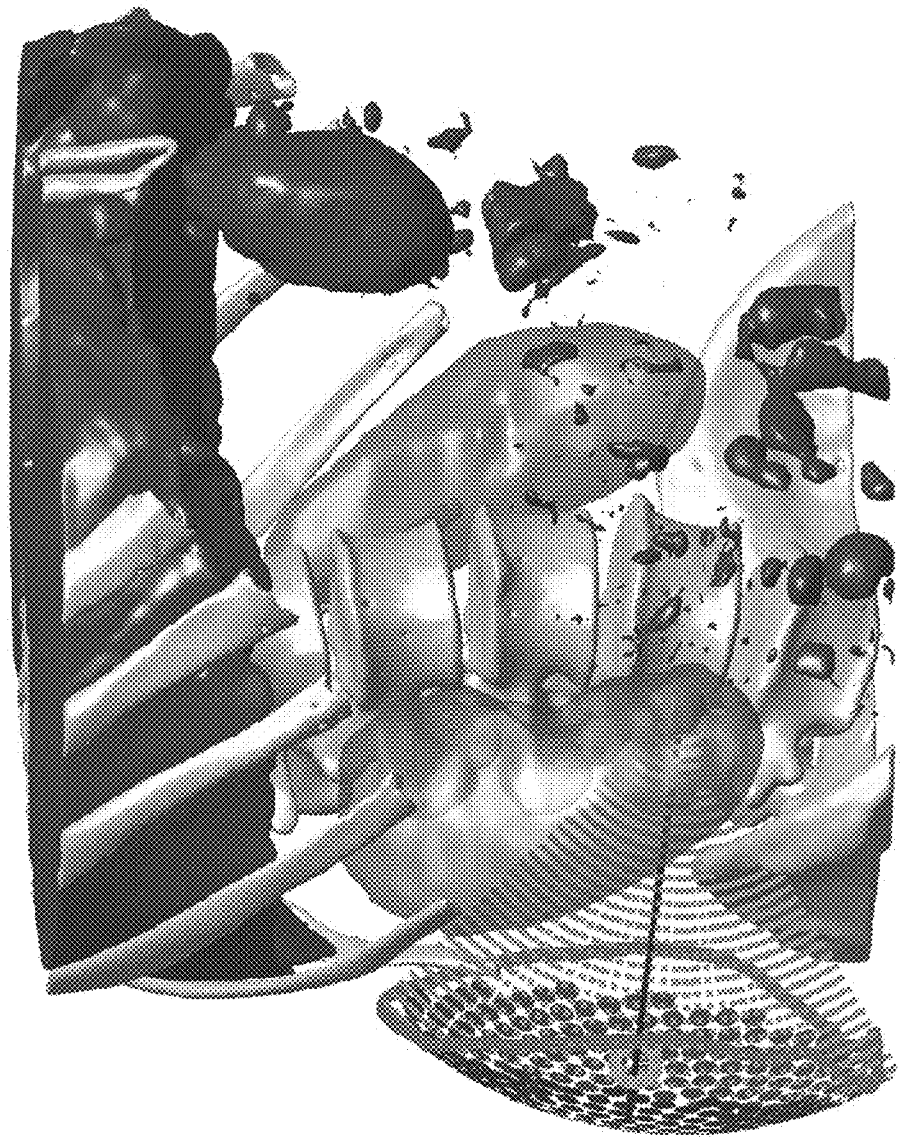
Figure 8C:
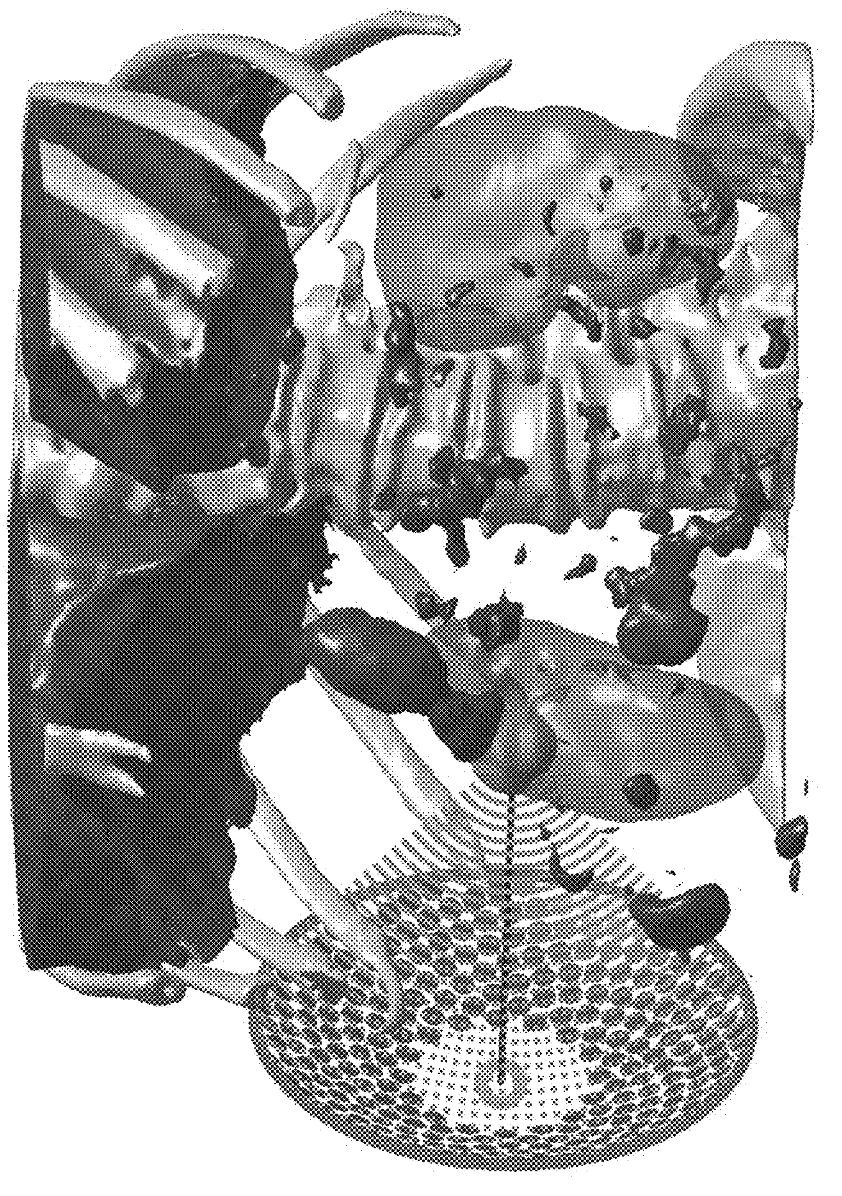

FIGS. 8A-8C illustrate optimized sonication geometries for test cases in accordance with an embodiment of the present technology. In particular, red contours represent the intersection of the focusing cone and the skin, while the green circles indicate the intersection of the HIFU array axis and the skin. Different tissue types are displayed using different colors: "tumor", "kidney", "bone", and "gas". The transducer positions are selected following the steps described above.

Case 1 had the most unobstructed acoustic window (FIG. 8A), because the focusing cone does not contain bones and gas structures, and it has a low fat percentage of 16% vol. The angle between the array axis and a normal of the skin surface is close to zero $\gamma=0.5°$, and the intersection parameter was close to unity $\sigma=1.13$.

Acoustic window is more challenging in FIG. 8B since the right hip bone intersected the beam path resulting in 1.3% vol., and 19% surf. for the "radial bones" parameter. In addition, the focusing cone contains 28% vol. of fat. However, the beam incidence is close to normal: $\gamma=1.7°$, and $\sigma=1.09$.

In FIG. 8C, the depth of tumor location is slightly greater than the focal length of the transducer. Thus, the geometry of the acoustic model has to be altered, with the transducer aperture being shifted 25 mm under the skin surface. This can be practical in at least some cases, as this would be analogous to patient positioning maneuvers commonly performed in surgery and focal therapies to reduce the depth of the target. The shift of the HIFU array results in a smooth contact between the active spherical surface of the array and skin surface, thus the beam incidence is normal: $\gamma=0°$, and $\sigma=1$. The challenging factors were high percentage of fat (81% vol.) and the presence of ribs (0.3% vol. and 5% surf.) inside the focusing cone.

Figures 9A, 9B:
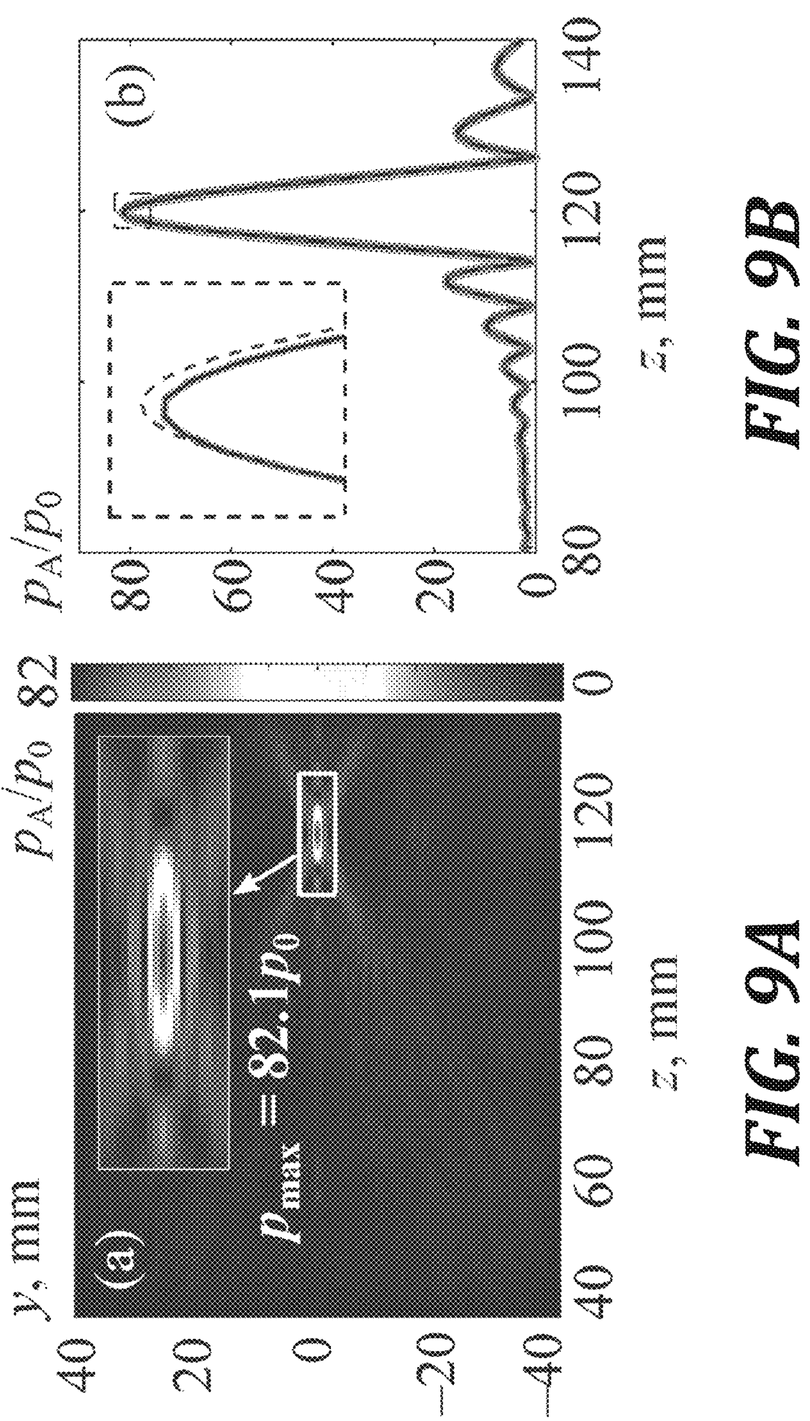
FIGS. 9A-9D illustrate normalized pressure amplitude in accordance with an embodiment of the present technology.
Figures 9C, 9D:
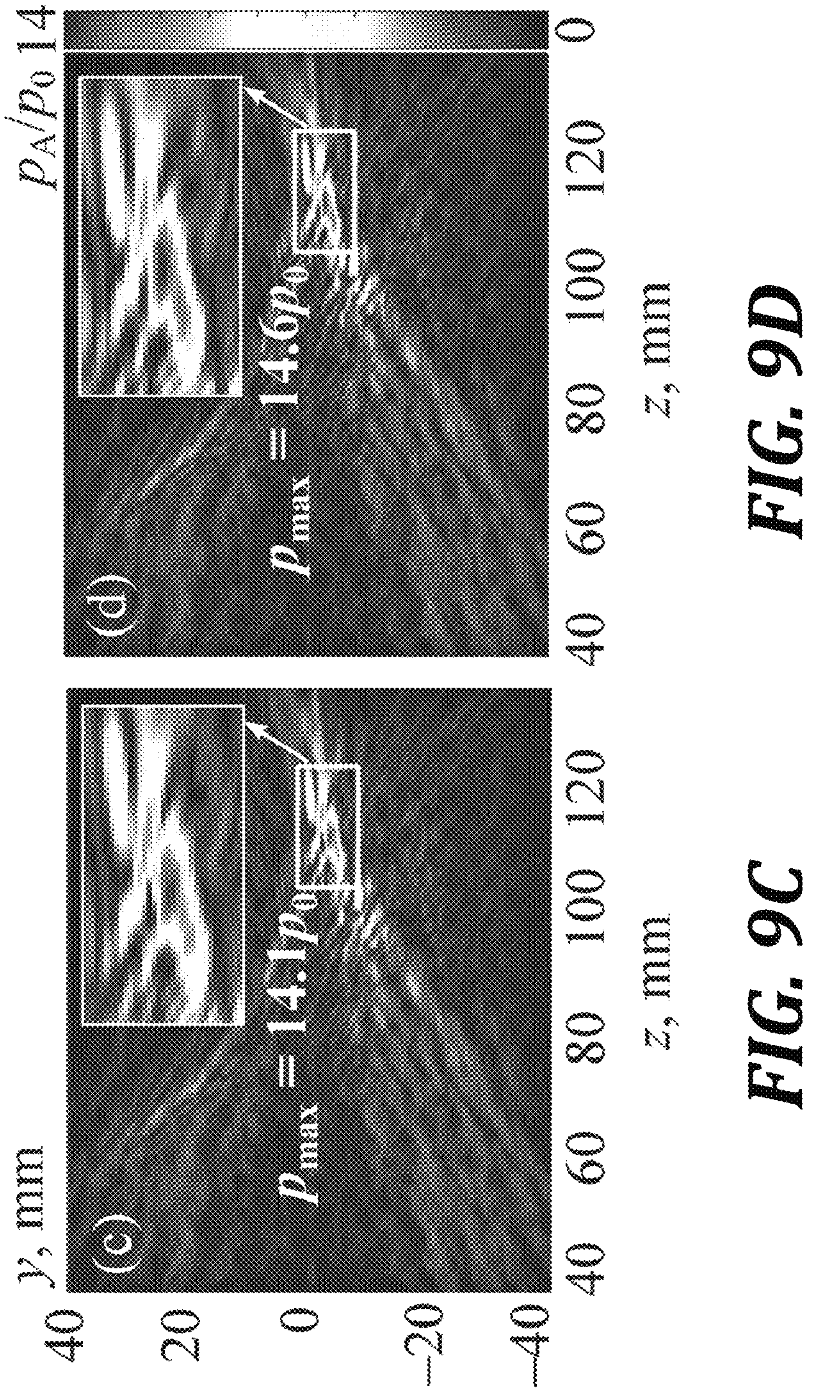

FIGS. 9A-9D illustrate normalized pressure amplitudes in accordance with an embodiment of the present technology. In particular, FIG. 9A illustrates the analytical Rayleigh integral solution for the normalized pressure amplitude $p_A/p_0$ in the axial plane zy for the case of focusing in water. FIG. 9B illustrates comparison of the solutions at the array axis z obtained using the analytical Rayleigh integral (dashed line), and k-Wave method with CFLs of 0.3 and 0.1 (thick and thin lines, respectively). FIGS. 9C and 9D illustrate k-Wave solutions in heterogeneous medium obtained with CFLs of 0.3 (FIG. 9C) and 0.1 (FIG. 9D). The labels $p_{max}$ indicate the maximum pressure value corresponding to the characteristic initial pressure at the elements, $p_0$.

The simulation steps and boundary condition, chosen above were validated in water and in Case 1 of FIG. 3A. First, the HIFU array field is calculated in water, with uniform boundary condition, and compared to the analytical solution. The k-Wave simulation results with CFL numbers of 0.3 and 0.1 are compared with the analytical solution. FIG. 9A shows the analytical solution for the normalized pressure amplitude $p_A/p_0$ in the axial plane zy, where $p_A=|P|$, $p_0$ is the pressure at the elements. A good agreement between the numerical and analytical (FIG. 9B, dashed line) solutions is achieved in both cases: the difference in the maximum pressure amplitudes $p_{max}$ is less than 1%. The difference in $p_{max}$ between the cases of CFL=0.3 and 0.1 is less than 0.001%.

The effect of the CFL number is slightly stronger for a heterogeneous medium. The focusing of the array with uniform boundary condition is simulated with the same two CFLs for Case 1. Although the pressure amplitude patterns for CFLs of 0.3 and 0.1 were similar (FIGS. 9C and 9D, respectively), there was a minor difference in $p_{max}$ and the positions of the maximum. The position of the maximum differed by 0.3 mm and 0.9 mm along the y, and z coordinates, and $p_{max}$ differed by 3.6%. Such accuracy was considered sufficient for the aims of this study, thus CFL=0.3 may be used for all other k-Wave simulations.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. A method for planning a sonication treatment of a target in a body, the method comprising:

obtaining a 3D anatomical model of the target and a portion of the body that is disposed between an ultrasound transducer and the target, wherein the ultrasound transducer is a phased array ultrasound transducer comprising a plurality of elements;

selecting a position of the ultrasound transducer by applying a transducer positioning algorithm for optimizing a sonication geometry;

simulating an aberrated ultrasound field at the target, wherein the aberrated ultrasound field is a linear high-intensity focused ultrasound (HIFU) field; and compensating for phase aberrations of the aberrated ultrasound field by:

backpropagating an ultrasound field from a virtual point source at the target, through the portion of the body that is disposed between the ultrasound transducer and the target, toward the ultrasound transducer, wherein the ultrasound field is spherical at the virtual point; and based on backpropagating the ultrasound field from the virtual point, determining time delays at the elements of the ultrasound transducer, wherein the time delays are configured for compensating the phase aberrations of the ultrasound field at the virtual point source.

2. The method of claim 1, wherein a first location of an initial target at the virtual point source at the target is different from a second location of a final target obtained with the time delays at the elements of the ultrasound transducer.

3. The method of claim 2, wherein the time delays are configured for generating a maximum pressure field at the final target.

4. The method of claim 2, the time delays of each element are configured based on a non-uniform phase distribution over each element.

5. The method of claim 1, wherein the transducer positioning algorithm comprises:

setting an orientation of the ultrasound transducer to avoid gas and to minimize a volume percentage of bones inside a focusing cone;

determining a parameter space within which a volume percentage of gas and the volume percentage of bones are approximately the same;

adjusting the orientation of the ultrasound transducer to minimize a surface area percentage of bones;

adjusting the orientation of the ultrasound transducer within a narrowed parameter space to minimize a volume percentage of fat inside the focusing cone;

adjusting the orientation of the ultrasound transducer within the narrowed parameter space to minimize distortion of an intersection contour; and within the narrowed parameter space, automatically finding a local minimum of an angle between an array axis and a normal to a skin surface.

6. The method of claim 5, wherein the transducer positioning algorithm is configured for:

minimizing interference with bones and fat tissue along a beam path; and achieving a normal incidence of an ultrasound beam on the skin surface.

7. The method of claim 1, wherein compensating for the phase aberrations is based on an ordinary least squares (OLS) optimization of phases at the elements of the ultrasound transducer.

8. The method of claim 1, further comprising:

applying a high-intensity focused ultrasound (HIFU) by the ultrasound transducer, wherein the elements of the ultrasound transducer are activated in accordance to the time delays.

9. The method of claim 1, further comprising:

setting boundary conditions for simulating the aberrated ultrasound field at the target.

10. The method of claim 1, further comprising:

selecting a shape and a size of the ultrasound transducer.

11. The method of claim 1, wherein the 3D anatomical model is obtained by:

a computed tomography (CT);

a magnetic resonance imaging (MRI); or a three-dimensional (3D) ultrasound visualization.

12. The method of claim 1, wherein the target is separated by soft tissue from the ultrasound transducer.

13. The method of claim 12, wherein the target is:

a prostate;

a liver;

a kidney;

a pancreas, or a breast of a patient.

14. The method of claim 1, wherein the target is located within an abdominal area of the body.

15. A system for sonication planning of a target in a body, the system comprising:

a phased array ultrasound transducer comprising a plurality of elements, each element being configured for emitting ultrasound at a selected phase; and a controller configured for:

obtaining a 3D anatomical model of the target and a portion of the body that is disposed between the ultrasound transducer and the target;

selecting a position of the ultrasound transducer by applying a transducer positioning algorithm for optimizing a sonication geometry;

simulating an aberrated ultrasound field at the target, wherein the aberrated ultrasound field is a linear high-intensity focused ultrasound (HIFU) field; and compensating for phase aberrations of the aberrated ultrasound field by:

backpropagating an ultrasound field from a virtual point source at the target, through the portion of the body that is disposed between the ultrasound transducer and the target, and toward the ultrasound transducer, wherein the ultrasound field is spherical at the virtual point; and based on backpropagating the ultrasound field from the virtual point, determining time delays at the elements of the ultrasound transducer, wherein the time delays are configured for compensating the phase aberrations of the ultrasound field at the virtual point source.

16. The system of claim 15, wherein the controller is further configured for:

setting boundary conditions for simulating the aberrated ultrasound field at the target.

17. The system of claim 15, wherein the controller is further configured for:

minimizing interference of bones and fat tissue along a beam path; and achieving a normal incidence of an ultrasound beam on skin surface.

18. The system of claim 15, wherein the controller is further configured for:

setting an orientation of the transducer to avoid gas and to minimize a volume percentage of bones inside a focusing cone;

determining a parameter space within which a percentage of gas and bones is approximately the same;

adjusting the orientation of the transducer to minimize a surface area percentage of bones;

adjusting the orientation of the transducer within a narrowed parameter space to minimize a volume percentage of fat inside the focusing cone;

adjusting the orientation of the transducer within the narrowed parameter space to minimize distortion of an intersection contour; and within the narrowed parameter space, automatically finding a local minimum of an angle between an array axis and a normal to the skin surface.

19. The system of claim 15, wherein the controller is further configured for determining the time delays of each element based on a non-uniform phase distribution over each element.

20. The system of claim 15, wherein the compensating for the phase aberrations is based on an ordinary least squares (OLS) optimization of phases at the elements of the ultrasound transducer.

21. The system of claim 15, wherein the 3D anatomical model is obtained by:

a computed tomography (CT);

a magnetic resonance imaging (MRI); or a three-dimensional (3D) ultrasound visualization.

22. The system of claim 15, wherein the target is obstructed by a layer of fat tissue.

* * * * *